(12) United States Patent
Koochekpour et al.

(10) Patent No.: US 7,166,691 B2
(45) Date of Patent: Jan. 23, 2007

(54) SAPOSIN C AND RECEPTORS AS TARGETS FOR TREATMENT OF BENIGN AND MALIGNANT DISORDERS

(75) Inventors: Shahriar Koochekpour, New Orleans, LA (US); A. Oliver Sartor, New Orleans, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 411 days.

(21) Appl. No.: 10/324,993

(22) Filed: Dec. 20, 2002

(65) Prior Publication Data

US 2004/0120961 A1    Jun. 24, 2004

(51) Int. Cl.
*A61K 38/00* (2006.01)
*C07K 1/00* (2006.01)
*A01N 37/18* (2006.01)

(52) U.S. Cl. .................... 530/300; 530/350; 514/2
(58) Field of Classification Search ............ 530/300, 530/350, 395; 424/184.1; 514/2
See application file for complete search history.

(56) References Cited

U.S. PATENT DOCUMENTS

| | | | |
|---|---|---|---|
| 5,191,067 A | 3/1993 | Lappi et al. | 530/399 |
| 5,478,804 A | 12/1995 | Calabresi et al. | 514/2 |
| 5,576,288 A | 11/1996 | Lappi et al. | 514/2 |
| 5,679,637 A | 10/1997 | Lappi et al. | 514/2 |
| 5,696,080 A | 12/1997 | O'Brien et al. | 514/2 |
| 5,700,909 A | 12/1997 | O'Brien | 530/326 |
| 5,714,459 A | 2/1998 | O'Brien et al. | 514/2 |

(Continued)

OTHER PUBLICATIONS

Jain, "Barriers to drug delivery in solid tumors", Sci Am. 171(1): 58-65, 1994.*

(Continued)

*Primary Examiner*—Larry R. Helms
*Assistant Examiner*—Hong Sang
(74) *Attorney, Agent, or Firm*—Bonnie J. Davis; John H. Runnels

(57) ABSTRACT

Saposin C was shown to be a trophic factor for a variety of cancer cells, e.g., prostate, lung, breast, and colon cancer cells. These cells expressed saposin C and responded to saposin C by increased levels of cell proliferation, cell migration, and cell invasion. Such activities typify and promote the neoplastic process. For prostate cancer, the androgen-insensitive prostate cancer cells responded to saposin C by higher levels of cell proliferation, cell migration and cell invasion than did the androgen-sensitive prostate cells. Stromal cells (from the prostate) were also responsive to saposin C-mediated signals in a manner typical of growth promoting compounds. The androgen-insensitive prostate cells were stimulated by saposin C to express higher levels of the urokinase plasminogen activator (uPA) and its receptor (uPAR), two proteins known to be involved in cell invasion. A conjugate of a peptide of the active region of saposin C (TX14A) and a toxin (saporin) was made and was shown to decrease the survival of prostate cancer cells, and the other cancer cells that were found to express saposin C (including cancers cells of the breast, colon, and lung). This conjugate or a compound of analogous action that inhibits cellular growth acting via a saposin-C binding receptor can be used to decrease tumor growth and/or treat disorders of stromal proliferation (e.g., benign prostatic hyperplasia, atherosclerosis, and vascular restenosis).

17 Claims, 16 Drawing Sheets

U.S. PATENT DOCUMENTS

| | | | |
|---|---|---|---|
| 6,268,347 B1 | 7/2001 | O'Brien | 514/14 |
| 6,326,467 B1 | 12/2001 | Net et al. | 530/328 |
| 6,348,194 B1 * | 2/2002 | Huse et al. | 424/143.1 |
| 6,420,126 B1 | 7/2002 | Huse et al. | 435/7.23 |

OTHER PUBLICATIONS

Freshney, Culture of Animal Cells, A Manual of Basic Technique, Alan R. Liss, Inc., 1983, New York, pp. 3-4.*

Dermer, Bio/Technology, 1994, 12:320.*

Andreasen, P. et al., "The urokinase-type plasminogen activator system in cancer metastasis," Int. J. Cancer, vol. 72, pp. 1-22 (1997).

Andreasen, P.A. et al., "Plasminogen activator inhibitors: hormonally regulated serpins," Mol. and Cell. Endocrinol., vol. 68, pp. 1-19 (1990).

Blasi et al., "Urokinase-type plasminogen activator: proenzyme, receptor and inhibitors," J Cell Biol., vol. 104, pp. 801-804 (1987).

Brunner, N. et al., "The urokinase plasminogen activator receptor in blood from healthy individuals and patients with cancer," APMIS, vol. 107, pp. 160-167 (1999).

Byrne, R.L. et al., "Peptide growth factors in the prostate as mediators of stromal epithelial interaction," Br. J. Urol., vol. 77, pp. 627-633 (1996).

Campana, W. et al., "Prosaptide activates the MAPK pathway by a G-protein-dependent mechanism essential for enhanced sulfatide synthesis by Schwann cells," FASEB J., vol. 3, pp. 307-314 (1998).

Chang, M.H.Y. et al., "Saposins A, B, C, and lysosomal storage disorders,"Clin. Chem, vol. 46, pp. 167-174 (2000).

Cherry, J.P. et al., "Analysis of cathepsin D forms and their clinical implications in prostate cancer," J. Urol., vol. 160. pp. 2223-2228 (1998).

Chiarodo, A., "National Cancer Institute roundtable on prostate cancer: future research directions," Cancer Res., vol. 51, pp. 2498-2505 (1991).

Chung, L.W., "The role of stromal-epithelial interaction in normal and malignant growth," Cancer Surveys, vol. 23, pp. 33-42 (1995).

Chung, L.W.K. et al., "Prostate epithelial differentiation is dictated by its surrounding stroma," Mol. Biol. Reports, vol. 23, pp. 13-19 (1996).

Dano, K. et al., "Cancer invasion and tissue remodeling-cooperation of protease systems and cell types," APMIS, vol. 107, pp. 120-127 (1999).

Davol, P. et al., "Targeting human prostatic carcinoma through basic fibroblast growth factor receptors in an animal model: characterizing and circumventing mechanisms of tumor resistance," The Prostate, vol. 40, pp. 178-191 (1999).

Davol, P. et al., "The mitotoxin, basic fibroblast growth factor-saporin, effectively targets human prostatic carcinoma in an animal model," J. Urol., vol. 156, pp. 1174-1179 (1996).

Festuccia, C. et al., "Plasminogen activation system modulates invasive capacity and proliferation in prostatic tumor cells," Clin. Exp. Metastasis, vol. 16, pp. 513-528 (1998).

Gaylis et al., F., "Plasminogen activators in human prostate cancer cell lines and tumors: correlation with the aggressive phenotype," J. Urol., vol. 142, pp. 193-198 (1989).

Gnanapragasam, V. et al., "Androgen receptor signaling in the prostate," Br. J. Urol., vol. 86, pp. 1001-10013 (2000).

Guo, C. et al., "Mitogenic signaling in androgen sensitive and insensitive prostate cancer cells," J. Urol., vol. 163, pp. 1027-1032 (2000).

Henry, J.A. et al., "Prognostic significance of the estrogen-related protein, cathepsin D, in breast cancer," Cancer, vol. 65, pp. 265-271 (1990).

Hiraiwa, M. et al., "Cell death prevention, mitogen-activated protein kinase stimulation, and increased sulfatide concentration in Schwann cells and oligodendrocytes by prosaposin and prosaptides," Proc.Natl.Acad.Sci. USA, vol. 94, pp. 4778-4781 (1997).

Hiraiwa, M. et al. "Lysosomal proteolysis of prosaposin, the precursor of saposins (sphingolipid activator proteins): its mechanisms and inhibition by ganglioside." Arch Biochem. Biophys., vol. 341, pp. 17-24 (1997).

Hiraiwa, M. et al., "Prosaposin receptor: evidence for a G-protein associated receptor", Biochem. Biophys. Res. Commun., vol. 240, pp. 415-418 (1997).

Lamharzi, N. et al., "Decreased in the level and mRNA expression of LH-RH and EGF receptors after treatment with LH-RH antagonist Cetrorelix in DU-145 prostate tumor xenografts in nude mice," Int. J. Oncol., vol. 13, pp. 429-435 (1998).

Lappi, D. et al., "Entering through the doors of perception: characterization of a highly selective substance P receptor-targeted toxin," Neuropeptides, vol. 34, pp. 323-328 (2000).

Lin, D.-l. et al., "Interleukin-6 induces androgen responsiveness in prostate cancer cells through up-regulation of androgen receptor expression," Clin. Cancer Res., vol. 7, pp. 1773-1781 (2001).

Liotta, L. et al., "Effect of plasminogen activator (urokinase), plasmin, and thrombin on glycoprotein and collagenous components on basement membrane," Cancer Res., vol. 41, pp. 4629-4634 (1981).

Makar, R. et al., "Immunohistochemical analysis of cathepsin D in prostate carcinoma," Modern Pathol., vol. 7, pp. 747-751 (1994).

Mayagarden, S. et al., "Evaluation of cathepsin D and epidermal growth factor receptor in prostate carcinoma," Modern Pathol., vol. 7, pp. 930-936 (1994).

McConnell, J.D. et al., "Benign prostatic hyperplasia: Diagnosis and Treatment," Clinical Practice Guideline, No. 8, AHCPR Publication No. 94-0582, Agency for Health Care Policy and Research, Public Health Service, U.S. Department of Health and Human Service, Rockville, Maryland, 166 pages (1994).

Misasi, R. et al., "Prosaposin treatment induces PC12 entry in the S phase of the cell cycle and prevents apoptosis: activation of ERKs and sphingosine kinase," FASEB. J., vol. 15, pp. 467-474.

Misasi, R. et al., "Prosaposin prosapeptide, a peptide form prosaposin induce an increase in ganglioside content on NS20Y neuroblastoma cells," Glycoconjugate J., vol. 13, pp. 195-202 (1996).

Mohler, J. et al., "Androgen and glucocorticoid receptors in the stroma and epithelium of prostatic hyperplasia and carcinoma," Clin. Cancer Res., vol. 2, pp. 889-895 (1996).

Morales, C.R. et al., "Distribution of mouse sulfated glycoprotein-1 (Prosaposin) in the testis and other tissues," J. Androl. vol. 19, pp. 156-164 (1998).

Morales, C.R. et al., "Expression and tissue distribution of rat sulfated glycoprotein-1 (prosaposin)," J. Histochem. Cytochem., vol. 44, pp. 327-337 (1995).

Morales, C.R. et al., "Role of prosaposin in the male reproductive system effect of prosaposin inactivation on the testis, epididymis, prostate, and seminal vesicles, " Arch. Androl., vol. 44, pp. 173-186 (2000).

Morales, C.R. et al., "Targeted disruption of the mouse prosaposin gene affects the development of the prostate gland and other male reproductive organs," J. Androl.. vol. 21, pp. 765-775 (2000).

Mordente, J.A. et al., "Hydrolysis of androgen receptor by cathepsin D: its biological significance in human prostate cancer," Br. J. Urol., vol. 82, pp. 431-435 (1998).

Murphy, G. et al., "The role of plasminogen activators in the regulation of connective tissue metalloproteinases," Ann, N.Y. Acad. Sci., vol. 667, pp. 1-12 (1992).

O'Brien, J.S. et al., "Identification of prosaposin as a neurotrophic factor," Proc Natl Acad Sci USA, vol. 91, pp. 9593-9596 (1994).

O'Brien, J.S. et al., "Identification of the neurotrophic sequence of prosaposin," FASEB. J., vol. 9, pp. 681-685 (1995).

Plonowski, S. et al., "Inhibition of PC-3 human androgen-independent prostate cancer and its metastasis by cytotoxic somatostatin analogue AN-238," Cancer Res., vol. 59, pp. 1947-1953 (1999).

Reuning, U. et al., "Multifunctional potential of the plasminogen activation system in tumor invasion and metastasis," Int. J. Oncology, vol. 13, pp. 893-906 (1998).

Sano, A. et al., "Sphingolipid hydrolase activator proteins and their precursors," Biochem. Biophys. Res. Comm., vol. 165, pp. 1191-1197 (1989).

Scott, W. et al., "Hormonal therapy of prostate cancer," Cancer, vol. 45, pp. 1929-1936 (1980).

Seger, R. et al., "The MAPK signaling cascade," FASEB J., vol. 9, pp. 726-735 (1995).

Upadhyay, J. et al., "Membrane type 1-matrix metalloproteinase (MT1-MMP) and MMP-2 immunolocalization in human prostate: change in cellular localization associated with high-grade prostatic intraepithelial neoplasia," Clin. Cancer Res., vol. 5, pp. 4105-4110 (1999).

Vihinen, P. et al., "Matrix metalloproteinases in cancer: prognostic markers and therapeutic targets," Int. J. Cancer, vol. 99, pp. 157-166 (2002).

Wilson, M.J. et al., "Immunocytochemical localization of cathepsin D in rat ventral prostate: evidence for castration-induced expression of cathepsin D in basal cells," Anat. Rec., vol. 229, pp. 321-333 (1991).

Wood, M. et al., "*In situ* hybridization studies of metalloproteinases 2 and 9 and TIMP-1 and TIMP-2 expression in human prostate cancer," Clin. Exp. Metastasis, vol. 15, pp. 246-258 (1996).

* cited by examiner

Cell Lysate  Prosaposin

Saposin C

Supernatant  Prosaposin

SAPOSIN C AND RECEPTORS AS TARGETS FOR TREATMENT OF BENIGN AND MALIGNANT DISORDERS

This invention pertains to a method of targeting prosaposin and saposin C, receptors for saposin C, and its signaling pathways in the treatment of cancer and other disorders of cell growth including stromal cell hyperplasia.

Molecular targets are increasingly important in the development of drugs to treat diseases. A molecular target provides a focus for development of new drugs by guiding investigators to specifically designed molecules that interfere with these targets in a desired manner. Multiple examples of targeted therapies being successful in disorders of cellular growth are now established. See M. S. Tallman, "Advancing the treatment of hematologic malignancies through the development of targeted interventions," Semin. Hematol., vol. 39, Suppl. 3, pp. 1–5 (2002); and L. Gianni, "The future of targeted therapy: combining novel agents," Oncology, vol. 63, Suppl. 1, pp. 47–56 (2002).

Disorders of prostate growth, including both prostate cancer and benign prostatic hyperplasia (BPH), affect over 500,000 men each year. Prostate cancer is a major public health problem worldwide, and is second only to lung cancer as the leading cause of death in males.

Benign prostatic hyperplasia (BPH) is characterized clinically by enlargement of the prostate gland with obstruction to the flow of urine, and pathologically by the proliferation of prostate epithelial and stromal (e.g., fibroblasts and smooth muscle) cells. A major cause for BPH-related prostate enlargement is the increased stromal volume of the prostate gland. BPH and its related signs and symptoms are extremely common among aging men. The prevalence of BPH increases constantly with age to 80–90% in men aged 80 to 90. According to the estimates based on the Agency for Health Care Policy and Research (AHCPR), approximately 5.6 million men aged 50 to 79 years would meet the AHCPR guidelines for treatment of BPH. See J. D. McConnell et al., "Benign prostatic hyperplasia: Diagnosis and Treatment," Clinical Practice Guideline, Number 8, AHCPR Publication No. 94-0582, Agency for Health Care Policy and Research, Public Health Service, U.S. Department of Health and Human Service, Rockville, Md. (1994). Normal, benign, and neoplastic growth in the prostate is largely dependent on interactions between stromal and epithelial cells. See L. W. Chung, "The role of stromal-epithelial interaction in normal and malignant growth," Cancer Survey, vol. 23, pp. 33–42 (1995). The impact of medical treatment on inhibition of BPH progression is becoming apparent. Identification of the molecules that influence the growth or proliferation of prostate epithelial and stromal cells in BPH can lead to the development of alternative therapeutic approaches.

There are other known disorders of stromal cell proliferation, especially proliferation of the smooth muscle cells. For example, smooth muscle cell proliferation is a dominant event in both atherosclerosis and vascular restenosis. See S. M. Schwartz, "Smooth muscle proliferation in hypertension. State-of-the-art lecture," Hypertension, vol. 6, pp. I56–61 (1984); and E. R. O'Brien et al., "Proliferation in primary and restenotic coronary atherectomy tissue. Implications for antiproliferative therapy," Cir. Res., vol. 73, pp. 223–231 (1993). Moreover, the pattern of mRNA expression associated with smooth muscle cell proliferation of BPH is similar to the pattern seen in proliferating smooth muscle cells in atherosclerosis. See V. K. Lin et al., "Myosin heavy chain gene expression in normal and hyperplastic human prostate tissue," Prostate, vol. 44, pp. 193–203 (2000). These references suggest that agents that target stromal cell proliferation can be used to treat BPH, atherosclerosis, and vascular restenosis.

Although the knowledge that most prostate cancers are androgen-dependent has been available for many decades, strategies of treatment using androgen and its signaling pathways as a molecular target have inevitably resulted in treatment failure. Although in the initial treatment phases, prostate cancer is primarily androgen-sensitive, the cancer becomes androgen-independent over time. In addition, androgen-sensitive prostate stromal cells are important in prostate cancer growth and progression. A number of hormones, peptide-hormones, and polypeptide growth factors (e.g., EGF (epithelial growth factor), TGF-$\alpha$ and -$\beta$ (transforming growth factor alpha and beta), IGF-I and -II (insulin-like growth factor one and two), and bFGF (basic fibroblast growth factor)) have been implicated in the growth and differentiation of prostate cancer cells.

The prostate gland requires androgens and growth factors for proliferation and maintenance of its function. Prostate development is dependent on androgens, and normal prostate secretory epithelial cells undergo apoptosis in the absence of androgens. See V. Gnanapragasam et al., "Androgen receptor signaling in the prostate," Br. J. Urol., vol. 86, pp. 1001–10013 (2000). In a normal prostate gland, androgen ablation results in the involution of the prostate epithelium.

Prostate cancer cells are initially dependent on androgen for growth. This stage of androgen-dependent prostate cancer can be treated with androgen-deprivation methods, such as castration or administering anti-androgen drugs. However, in patients who have undergone prolonged anti-androgen drug therapy, the prostate cancer cells acquire the ability to proliferate in the absence of androgen. (V. Gnanapragasam et al., 2000). Moreover, a progression to androgen-independent prostate cancer (the advanced stage of the disease), for which there are no satisfactory treatments, normally occurs. Although androgen-independent, these later prostate cancer cells continue to express genes that are known to be stimulated by androgen, suggesting an androgen-independent activation of the androgen receptor (AR) signaling pathway. The androgen receptor (AR) is an essential mediator for the effect of androgen. It is unknown what physiological mechanisms are involved in the switch to androgen-independent cancer cells, and in the androgen-independent activation of the AR signaling pathway.

Prostate specific antigen (PSA) is a prostate specific tumor marker, and the most widely used marker for screening, diagnosing, and determining the prognosis of patients with prostate cancer throughout the world. Androgens are known regulators of PSA expression. However, even after androgen ablation, the PSA levels can increase and are used to suggest recurrent disease. Non-androgenic activation of androgen receptors leading to a stimulation of PSA expression has been reported, e.g., FGF-6 and IL-6 (interleukin-6). These known regulators of PSA expression contribute to a more malignant phenotype in prostate cancer. See D. -L. Lin et al., "Interleukin-6 induces androgen responsiveness in prostate cancer cells through up-regulation of androgen receptor expression," Clin. Cancer Res., vol. 7, pp. 1773–1781 (2001).

For a prostate cancer to progress to the androgen-independent stage requires an interaction among the cancer cells, the extracellular matrix proteins, and the nearby stromal cells. Androgen receptors are present in the prostate stromal cells, and prostate stromal cells are known to respond to androgens. See J. Mohler et al., "Androgen and glucocorticoid receptors in the stroma and epithelium of prostatic hyperplasia and carcinoma," Clin. Cancer Res., vol. 2, pp. 889–895 (1996). Prostate stromal cells also express a number of growth factors (i.e., EGF, TGF-β1, bFGF, VEGF) and possess receptors for the growth factors. See R. L. Byrne et al., "Peptide growth factors in the prostate as mediators of stromal epithelial interaction," Br. J. Urol., vol. 77, pp. 627–633 (1996). These findings indicate that prostate stromal cells are regulated by both androgen and growth factors known to be produced by cancer cells. In addition, the stromal cells play an important role in, the differentiation of prostate epithelial cells. See L. W. K. Chung et al., "Prostate epithelial differentiation is dictated by its surrounding stroma," Mol. Biol. Reports, vol. 23, pp. 13–19 (1996). In a similar manner, the stromal cells may play an important role in the multiple stages of prostate cancer invasion and metastasis.

During the complex process of tumor progression, prostate cancer often begins with androgen-sensitive cells of low virulence. After androgen deprivation, prostate cancers eventually transform into cells that are primarily androgen-insensitive. This transformation, in some cases, is a result of an outgrowth of AR-negative cells (cells lacking androgen receptors), resulting in the establishment of hormone resistance. In other cases, androgen-independence is associated with presence of androgen receptors that transmit growth signals in the absence of conventional steroid ligands. See A. Chiarodo, "National Cancer Institute roundtable on prostate cancer: future research directions," Cancer Res., vol. 51, pp. 2498–2505 (1991); and W. Scott et al., "Hormonal therapy of prostate cancer," Cancer, vol. 45, pp. 1924–1936 (1980).

The prostate gland and its secretions are known to contain a variety of potent compounds that interact with the surrounding extracellular matrix and stroma. In addition to growth factors and androgens, proteases have also been implicated in the transformation into malignant and androgen-independent phenotypes, and in the development of both normal and cancerous prostate cells. These proteases include (among others) plasminogen activators, matrix metalloproteinases (MMPs), and lysosomal cathepsins. The expression and activity of the proteases are known to be influenced by various growth factors and androgens. See P. Vihinen et al., "Matrix metalloproteinases in cancer: prognostic markers and therapeutic targets," hit. J. Cancer, vol. 99, pp. 157–166 (2002).

One important group of proteases in mammals is the plasminogen activators. Mammalian cells contain two types of plasminogen activators, the urokinase type (uPA) and the tissue type (tPA). Of the two, uPA is primarily involved in the extracellular matrix degradation involved in cancer cell invasion. See K. Dano et al., "Cancer invasion and tissue remodeling-cooperation of protease systems and cell types," APMIS, vol. 107, pp. 120–127 (1999). The uPA system consists of the serine proteases uPA and plasmin, two important serpin inhibitors (PAI-1 and PAI-2, respectively plasminogen activator inhibitor-1 and 2), and a uPA cell surface receptor (uPAR). See F. Blasi et al., "Urokinase-type plasminogen activator: proenzyme, receptor and inhibitors," J. Cell Biol., vol. 104, pp. 801–804 (1987). uPA has a restricted substrate specificity, functioning primarily in cleaving plasminogen to plasmin. See L. Liotta et al., "Effect of plasminogen activator (urokinase), plasmin, and thrombin on glycoprotein and collagenous components on basement membrane," Cancer Res., vol. 41, pp. 4629–4636 (1981). The plasmin then degrades extracellular matrix components and activates many pro-matrix metalloproteinases (MMPs). See G. Murphy et al., "The role of plasminogen activators in the regulation of connective tissue metalloproteases," Ann. N.Y. Acad. Sci., vol. 667, pp. 1–12 (1992). The plasminogen activation system is specifically controlled by the inhibitors, of which PAI-1 has a more important role in cancer invasion. See P. Andreasen et al., "The urokinase-type plasminogen activator system in cancer metastasis," Int. J. Cancer, vol. 72, pp. 1–22 (1997); and P. A. Andreasen et al., "Plasminogen activator inhibitors: Hormonally regulated serpins," Mol. Cell Endocrinol., vol. 88, pp. 1–19 (1990).

Both the secretion of uPA and the presence of receptor-bound uPA at the cell surface characterize prostate cancer cells that have the invasive phenotype. See F. Gaylis et al., "Plasminogen activators in human prostate cancer cell lines and tumors: correlation with the aggressive phenotype," J. Urol., vol. 142, pp. 193–198 (1989); and Blasi et al., "Urokinase-type plasminogen activator: proenzyme, receptor and inhibitors," J. Cell Biol., vol. 104, pp. 801–804 (1987). Plasminogen activation has been shown to play a key role in cancer invasion and metastasis. See K. Dano et al., 1999; and C. Festuccia et al., "Plasminogen activation system modulates invasive capacity and proliferation in prostatic tumor cells," Clin. Exp. Metastasis, vol. 16, pp. 513–528 (1998). Most of the degradation activity of uPA occurs while the protease is bound to uPAR, which focuses the digestion of the extracellular matrix into the area near the cell. In addition, the binding of uPA to its cell receptor activates a signal pathway inside the cell leading to possible activation of gene transcription. The modulatory effects of uPA on the migration, proliferation, and adhesion of the cell may be mediated by this signal-transduction pathway rather than by the proteolytic activity. See U. Reuning et al., "Multifunctional potential of the plasminogen activation system in tumor invasion and metastasis," Int. J. Oncology, vol. 13, pp. 893–906 (1998). In addition, a soluble urokinase receptor is released from tumors, and in cancer patients the blood levels of soluble receptor has been increased. See N. Brunner et al., "The urokinase plasminogen activator receptor in blood from healthy individuals and patients with cancer," APMIS, vol. 107, pp. 160–167 (1999).

Matrix metalloproteinases (MMPs) additionally play a significant role during the development and metastasis of prostate cancer. Prostate cancer cells secrete high levels of MMPs and low levels of endogenous MMP inhibitors (TIMPs), thus creating an excess balance of MMPs. In prostate cancer, in vivo studies have shown that high expression of MMP-2 by in situ hybridization was associated with aggressive behavior and metastasis. See J. Upadhyay et al., "Membrane type 1-matrix metalloproteinase (MT1-MMP) and MMP-2 immunolocalization in human prostate: change in cellular localization associated with high-grade prostatic intraepithelial neoplasia," Clin. Cancer Res., vol. 5, pp. 4105–4110 (1999); and M. Wood et al., "In situ hybridization studies of metalloproteinases 2 and 9 and TIMP-1 and TIMP-2 expression in human prostate cancer," Clin. Exp. Metastasis, vol. 15, pp. 246–258 (1996). A consistent change in localization and intracellular distribution of MMP-2 and MT1-MMP was associated with the transition from benign prostate epithelium to high-grade prostatic intraepithelial neoplasia, suggesting that regulation of these enzymes is altered during the early stages of tumor progression.

In prostate cancer a variety of ligands and receptors including G-protein-coupled receptors are known to activate the MAPK pathways. See C. Guo et al., "Mitogenic signaling in androgen sensitive and insensitive prostate cancer cells," J. Urol., vol. 163, pp. 1027–1032 (2000). Mitogen-activated protein kinases (MAPKs) are serine/threonine kinases that are activated by phosphorylation in response to a wide array of extracellular stimuli usually through a G-protein-associated cell membrane receptor. See R. Seger et al., "The MAPK signaling cascade," FASEB J., vol. 9, pp. 726–735 (1995). Three enzymes important in this pathway are MEK1/2 (mitogen-activated, ERK-activating kinase isoforms 1 and 2), ERK1/2 (extracellular regulated kinases with three forms—$p44^{MAPK}$, $p42^{MAPK}$, and $p40^{MAPK}$), and RSK (ribosomal S6 kinase, also $p90^{rsk}$). The phosphorylation activates MEK1/2 which then in turn phosphorylates and activates ERK1/2. The activated ERK1/2 then phosphorylates RSK, which then affects gene transcription or cell behavior.

Prosaposin (PSAP) is a 70 kilodalton glycoprotein and the precursor of a group of four smaller glycoproteins that are required for hydrolysis of glycosphinogolipids by lysosomal hydrolases. See U.S. Pat. Nos. 6,268,347, 5,714,459; 5,700,909; and 5,696,080. Prosaposin is known to be a neurotrophic factor located in several places: in the lysosomes of various cell types, in the plasma membranes of cells derived from neuro-glial tissues, and in body fluids as a secretory protein. In the male reproductive system, prosaposin has been found in seminiferous tubular fluid, in seminal plasma, and in prostatic secretions. See C. R. Morales et al., "Expression and tissue distribution of rat sulfated glycoprotein-1 (prosaposin)," J. Histochem. Cytochem., vol. 44, pp. 327–337 (1995); and C. R. Morales et al., "Distribution of mouse sulfated glycoprotein-1 (Prosaposin) in the testis and other tissues," J. Androl. vol. 19, pp. 156–164 (1998). Prosaposin is proteolytically processed (by cathepsin D) to generate four saposin proteins, A, B, C, and D, each about 8–13 kDa. These four proteins exist as adjacent tandem domains in the prosaposin polypeptide. See M. Hiraiwa et al., "Lysosomal proteolysis of prosaposin, the precursor of saposins (sphingolipid activator proteins): its mechanism and inhibition by ganglioside," Arch. Biochem. Biophys., vol. 341, pp. 17–24 (1997). Both prosaposin and mature saposins (A–D) are detectable in plasma samples of normal individuals, and saposins A, C, and D show a tight plasma distribution. See. M. H. Y. Chang et al., "Saposins A, B, C, and lysosomal storage disorders," Clin. Chem., vol. 46, pp. 167–174 (2000).

Neurotrophic factor activity of prosaposin resides in a 12 amino acid residue located in the $NH_2$-terminal portion of the saposin C domain. See J. S. O'Brien et al., "Identification of the neurotrophic sequence of prosaposin," FASEB J., vol. 9, pp. 681–685 (1995). This known sequence has been used to derive biologically active synthetic peptides (14–22 residues) called prosaptides, e.g., TX14A. See R. Misasi et al., "Prosaposin and prosapeptide, a peptide from prosaposin, induce an increase in ganglioside content on NS20Y neuroblastoma cells," Glycoconjugate J., vol. 13, pp. 195–202 (1996). Different neurobiological functions of prosaposin and saposin C, including prosaptides (i.e., TX14A), are mediated through a G-protein-associated cell membrane receptor. See W. Campana et al., "Prosaptide activates the MAPK pathway by a G-protein-dependent mechanism essential for enhanced sulfatide synthesis by Schwann cells," FASEB J., vol. 3, pp. 307–14 (1998). Saposin C, TX14A, and prosaposin have been found to affect the enzymes in the MAPK pathway via a G-protein dependent mechanism in a number of neuro-glial derived cells. See M. Hiraiwa et al., "Prosaposin receptor: evidence for a G-protein associated receptor," Biochem. Biophys. Res. Commun., vol. 240, pp. 415–418 (1997).

Targeted disruption of the mouse prosaposin gene has been shown to cause a number of abnormalities in male reproductive organs, including testicular atrophy, involution of the prostate, seminal vesicle and epididymis, absence of secretory cells of prostate, and inactivation of the MAP kinase pathway in prostate epithelium See C. R. Morales et al., "Targeted disruption of the mouse prosaposin gene affects the development of the prostate gland and other male reproductive organs," J. Androl., vol. 21, pp. 765–775 (2000); and C. R. Morales et al., "Role of prosaposin in the male reproductive system: effect of prosaposin inactivation on the testis, epididymis, prostate, and seminal vesicles," Arch. Androl., vol. 44, pp. 173–186 (2000).

The serine protease cathepsin D (Cath-D) which cleaves prosaposin to the four saposin molecules is highly expressed among some adenocarcinomas. The presence of Cath-D also has been correlated with a worse prognosis among some cancers. The expression of this protease in breast cancer cells is stimulated by estrogens. See J. A. Henry et al., "Prognostic significance of the estrogen-related protein, cathepsin D, in breast cancer," Cancer, vol. 65, pp. 265–271 (1990).

Cath-D is expressed in rat ventral prostate cells undergoing castration-induced apoptosis. See M. J. Wilson et al., "Immunocytochemical localization of cathepsin D in rat ventral prostate: evidence for castration induced expression of cathepsin D in basal cells," Anat. Rec., vol. 229, pp. 321–333 (1991). Using immunohistochemical staining, human primary prostate adenocarcinomas were shown to over express Cath-D, relative to benign prostate cells. See R. Makar et al., "Immunohistochemical analysis of cathepsin D in prostate carcinoma," Modem Pathol., vol. 7, pp. 747–751 (1994). Moderate to strong immunoreactivity with anti-cath-D was also detected in prostatic intraepithelial neoplasia, primary adenocarcinomas, and metastatic prostate cases. See S. Mayagarden et al., "Evaluation of cathepsin D and epidermal growth factor receptor in prostate carcinoma," Modem Pathol., vol. 7, pp. 930–936 (1994). Additionally, endogenous cath-D in an androgen-sensitive prostate cancer cell line (LNCaP) was found to hydrolyze the androgen receptor (AR), indicating a potential role for Cath-D in modulating AR function in prostate cancer. See J. A. Mordente et al., "Hydrolysis of androgen receptor by cathepsin D: its biological significance in human prostate cancer," Br. J. Urol., vol. 82, pp. 431–435 (1998).

Strong evidence suggests that growth factors and their receptors are necessary for the progression of neoplastic diseases and hyperplastic disorders. Treatment of certain cancers has been proposed by linking these growth factors with a toxin or by using other mechanisms designed to take advantage of the consequences of disrupting these targeted signaling pathway. In particular, conjugates containing the ribosomal toxin saporin and growth factors, such as bFGF have been proposed. See, U.S. Pat. Nos. 5,191,067; 5,478,804; 5,576,288; and 5,679,637. These conjugates attach to the cell receptor for the specific growth factor and are internalized by receptor-mediated endocytosis. Upon release of the conjugate from endosomes, the saporin toxin catalytically inhibits protein synthesis. The use of toxins derived from plants (i.e, Saporin) or bacteria (i.e, PE40) conjugated to antibodies, growth factors, cytokines or active peptides derived from cytokines or growth factors (e.g., fibroblast growth factor, transforming growth factor-α, interleukin 4, interleukin 6) have been demonstrated for a number different cancers to have antitumor or cell-killing effect. For example, it has been shown that bFGF-saporin effectively targets a number of human tumors expressing bFGF receptors, including melanoma, prostate carcinoma, ovarian teratocarcinoma, and neuroblastoma growing both in tissue culture and as xenografts in nude mice, but is not cytotoxic to cells that do not express FGF receptor. Additionally a group of gonadotropin-release hormone (GnRH)/toxin conjugate compounds have been proposed for treating certain sex hormone related diseases such as prostate or breast cancer. See U.S. Pat. No. 6,326,467.

Like the receptors for growth factors, G-protein-coupled receptors (GPCR) such as Prosaposin receptors, are one of the largest single class of receptors in biology and play a key role in a remarkably large number of physiological and pathological conditions. All of these receptors have one thing in common: when they bind to their ligand, they activate signaling pathways and then are internalized, sometimes rather rapidly, into the cells that express the receptor. A number of highly selective GPCR-targeted toxins have been tested for their cytotoxic effects in vitro and in vivo. See D. Lappi et al., "Entering through the doors of perception: characterization of a highly selective substance P receptor-targeted toxin," Neuropeptides, vol. 34, pp. 323–328 (2000); S. Plonowski et al., "inhibition of PC-3 human androgen-independent prostate cancer and its metastasis by cytotoxic somatostatin analogue AN-238," Cancer Res., vol. 59, pp. 1947–1953 (1999); N. Lamharzi et al., "Decrease in the level and mRNA expression of LH-RH and EGF receptors after treatment with LH-RH antagonist Cetrorelix in DU-145 prostate tumor xenografts in nude mice," Int. J. Oncol., vol. 13, pp. 429–435 (1998); P. Davol et al., "The mitotoxin, basic fibroblast growth factor-saporin, effectively targets prostatic carcinoma in an animal model," J. Urol., vol. 156, pp. 11794–11798 (1996); and P. Davol et al., "Targeting human prostatic carcinoma through basic fibroblast growth factor receptors in an animal model: characterizing and circumventing mechanisms of tumor resistance," Prostate, vol. 40, pp. 178–191 (1999). Activation of MAPK pathway by saposin C, its tropic peptide(s) or analogous compounds via a G-protein dependent mechanism has been found for a number of neuro-glial derived cells such as PC-12, Schwann and neuroblastoma cells. See M. Hiraiwa et al., "Cell death prevention, mitogen-activated protein kinase stimulation, and increased sulfatide concentration in Schwann cells and oligodendrocytes by prosaposin and prosaptides," Proc.Natl.Acad.Sci. USA, vol. 94, pp. 4778–4781 (1997); W. M. Campana et al., "Prosaptide activates the MAPK pathway by a G-protein-dependent mechanism essential for enhanced sulfatide synthesis by Schwann cells," FASEB. J., vol. 3, pp. 307–14 (1998); R. Misasi et al., "Prosaposin treatment induces PC12 entry in the S phase of the cell cycle and prevents apoptosis: activation of ERKs and sphingosine kinase," FASEB. J., vol. 15, pp. 467–474 (2001); J. S. O'Brien et al., "Identification of prosaposin as a neurotrophic factor," Proc Natl Acad Sci USA, vol. 91, pp. 9593–6 (1994); and M. Hiraiwa et al., "Prosaposin receptor: evidence for a G-protein associated receptor," Biochem. Biophys. Res. Commun., vol. 240, pp. 415–8 (1997).

We have shown that saposin C is a trophic factor for a variety of cancer cells, e.g., prostate, lung, breast, and colon cancer cells. These cells expressed saposin C and responded to saposin C by increased levels of cell proliferation, cell migration, and cell invasion. Such activities typify and promote the neoplastic process. For prostate cancer, the androgen-insensitive prostate cancer cells responded to saposin C by higher levels of cell proliferation, cell migration and cell invasion than did the androgen-sensitive prostate cells. Stromal cells (from the prostate) were also responsive to saposin C-mediated signals in a manner typical of growth promoting compounds. The androgen-insensitive prostate cells were stimulated by saposin C to express higher levels of the urokinase plasminogen activator (uPA) and its receptor (uPAR), two proteins known to be involved in cell invasion. A conjugate of a peptide of the active region of saposin C (TX14A) and a toxin (saporin) was made and was shown to decrease the survival of prostate cancer cells, and the other cancer cells that were found to express saposin C (including cancers cells of the breast, colon, and lung). This conjugate or a compound of analogous action that inhibits cellular growth acting via a saposin-C binding receptor can be used to decrease tumor growth and/or treat disorders of stromal proliferation (e.g., benign prostatic hyperplasia, atherosclerosis, and vascular restenosis). These data indicate that prosaposin signaling pathways are regulators of both epithelial and stromal growth and that prosaposin-signaling pathway can be exploited to diminish such growth by using targeted molecular approaches.

Figure 1A:
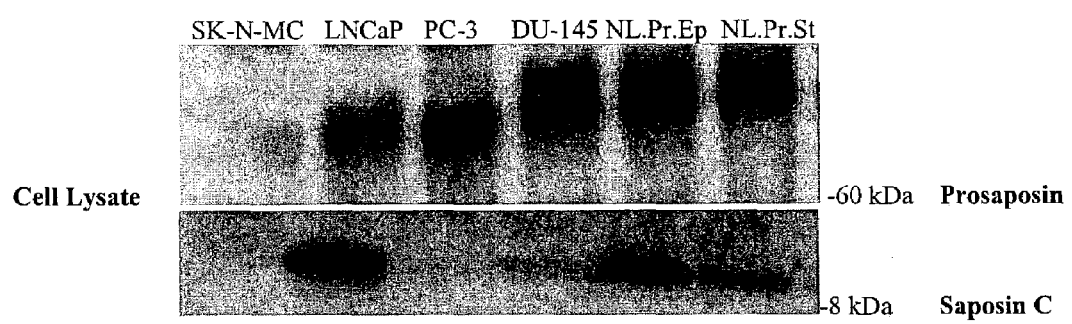
FIG. 1A illustrates the presence of prosaposin and saposin C in the intracellular fluid extracted from various cell lines, with the highest concentration of extracellular prosaposin found in prostate cell lines that are insensitive to androgen (two prostate cancer cell types designated PC-3 and DU-145 and normal prostate epithelial cells designated NI.Pr.Ep); and the highest concentration of intracellular saposin C found in prostate cell lines that are sensitive to androgen (a prostate cancer cell line designated LNCaP, and normal prostate epithelial cell line designated PrEp).

The present invention provides both a target molecule and a targeted signaling transduction pathway to use in disorders of either epithelial or stromal cell growth. We have demonstrated for the first time that the molecule saposin C is a trophic factor for all epithelial cancer cells assayed to date, e.g., prostate, lung, breast, and colon cancer cells. A conjugate of a toxin and either saposin C or peptides of the active region of saposin C (e.g., TX14A) can be used to target cancer cells to decrease growth. In addition, we have demonstrated that stromal cell growth signals can be upregulated by molecules of this class. The future applications of these observations are well known to those familiar with the field of therapeutics that target molecular signaling transduction pathways. Saposin C signaling transduction pathways are logical molecular targets for therapeutics designed to inhibit cancers or disorders of stromal growth (e.g., benign prostate hyperplasia, atherosclerosis, or vascular restenosis following vascular interventions). It is known that smooth muscle proliferation present in atherosclerosis and prostatic hyperplasia are similar suggesting that agents inhibiting growth of prostate smooth muscle would be inhibitory against vascular smooth muscle as well. See V. K. Lin et al., 2000. It is also known that smooth muscle cell proliferation in an atherosclerotic lesion is causal of vascular occlusion. See S. M. Schwartz, 1984. In addition, smooth muscle proliferation and endothelial proliferation are hallmarks of vascular restenosis in arteries following various interventions. See E. R. O'Brien et al., 1993.

An active region of saposin C has been identified at least for the neurotrophic activity of saposin C. The sequence of this active region has been used to derive synthetic peptides that are biologically active, called "prosaptides." An example of a prosaptide is the compound designated TX14A. We have demonstrated for the first time that a conjugate of a toxin and a prosaptide can also be used to decrease the growth of cells derived from epithelial cancer cells.

Saposin C, or compounds analogous to Saposin C (e.g., a prosaptide) can be modified or conjugated with another molecule such that cells normally responsive to a signaling transduction pathway initiated by Saposin C can now be subject to cytotoxic or cytostatic action. For example, Saposin C or a prosaptide can be conjugated to a cytotoxic agent so as to target the cytotoxic agent specifically to cells which exhibit cell receptors that bind to saposin C or a prosaptide. As used in the specification and claims, a "cytotoxic agent" includes all compounds that are capable of inhibiting cell function, e.g., a cytotoxic agent that inhibits protein synthesis.

Examples of cytotoxic agents include, but are not limited to, diphtheria toxin, ricin toxin, abrin toxin, pseudomonas exotoxin, shiga toxin, α-amanitin, pokeweek antiviral protein (PAP), ribosome-inhibiting protein (RIP), especially the ribosome inhibiting proteins of barley, wheat, flax, corn rye, gelonin, abrin, modeccin and certain cytotoxic chemicals such as, for example, melphalan, methotrexate, nitrogen mustard, doxorubicin and daunomycin. See U.S. Pat. Nos. 5,679.637 and 6,326,467. Also included would be any portion or active domain of any of the above listed cytotoxic agents, as described in U.S. Pat. No. 6,326,467. Additionally, ionizing radioisotopes would be examples of cytotoxic agents.

The ability to make conjugates of biological proteins or peptides and cytotoxic agents is well known in the art. See, e.g., U.S. Pat. Nos. 5,679,637 and 6,326,467 and their family members.

In addition, antagonists or agonists of Saposin C can be used to alter the signaling transduction pathway. The design of antagonists and agonist to known peptides is well known to those skilled in the art. As used in the specification and the claims, the term "Saposin-C agonist" refers to a substance or signal that directly or indirectly activates a receptor function similar to the activation by saposin C; and the term "Saposin-C antagonist" refers to a substance that directly or indirectly interferes with the function of a receptor that is activated by Saposin C. Typically, the effect of an antagonist is observed as a blocking of activation by an agonist. Antagonists include competitive and non-competitive antagonists. A competitive antagonist (or competitive blocker) interacts with or near the site specific for the agonist (e.g., ligand or neurotransmitter) for the same or closely situated site. A non-competitive antagonist or blocker inactivates the functioning of the receptor by interacting with a site other than the site that interacts with the agonist. Saposin-C agonists or antagonist can be identified by analyzing and comparing the binding characteristics with that of saposin C. Saposin-C agonists or antagonists can be designed by careful analysis of the required binding elements of the saposin-C receptor interaction and then substituting sterically acceptable functional groups that either augment or diminish those interactions. By several assays, molecules can be optimized to substitute for prosaposin in a potent manner or to block activation of saposin-C medicated events. In addition, computer based calculations that examine conformational consequences of such chemically substituted compounds can provide insight and speed the process of designing an appropriate agonists or antagonists that might be used as a drug. Such designer molecules can be nonpeptides. See R. M. Freidinger, "Nonpeptidic ligands for peptide and protein receptors," Curr. Opin. Chem. Biol., vol. 3, pp. 395–406 (1999).

The term "signal transduction pathway" as used in the Specification and claims means the biochemical pathways that transmit signals to the cell after a ligand-receptor interaction. The signal may vary according to the type of receptor studied and may include phosphorylation/dephosphorylation of the various proteins or activation of certain enzymes that modulate biochemical events such as cyclic AMP formation.

The term "therapeutically effective amount" as used herein refers to an amount of the saposin C, or an analogous compound capable of altering the signaling transduction pathway or other cellular effect (such as a prosaptide/toxin conjugate) in a manner sufficient to alter either tumor or stromal cell growth or to inhibit metastasis to a statistically significant degree ($p<0.05$). The term "therapeutically effective amount" therefore includes, for example, an amount sufficient to prevent the cancer cells from proliferating and/or invading the surrounding tissues and cells. The dosage ranges for the administration of the conjugate or other analogous compound are those that produce the desired effect. Generally, the dosage will vary with the age, weight, condition, sex of the patient, type of tumor, the degree of tumor development, and the degree of tumor metastasis. A person of ordinary skill in the art, given the teachings of the present specification, may readily determine suitable dosage ranges. The dosage can be adjusted by the individual physician in the event of any contraindications. In any event, the effectiveness of treatment can be determined by monitoring appropriate end points (e.g., the extent of a decrease in tumor size or in metastatic behavior) by methods well known to those in the field. Moreover, the effective compounds can be applied in pharmaceutically acceptable carriers known in the art. The application can be oral, by injection, or topical.

The saposin-C or prosaptide/toxin conjugate or signaling transduction pathway altering compound(s) may be administered to a patient by any suitable means, including orally, parenteral, subcutaneous, intrapulmonary, topically, and intranasal administration. Parenteral infusions include intramuscular, intravenous, intra-arterial, or intra-peritoneal administration. The effective compounds may also be administered transdermally, for example in the form of a slow-release subcutaneous implant, or orally in the form of capsules, powders, or granules. The effective compounds can also be targeted to the tumor cells by direct application to the tumor.

Pharmaceutically acceptable carrier preparations for parenteral administration include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient maybe mixed with excipients that are pharmaceutically acceptable and are compatible-with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The form may vary depending upon the route of administration. For example, compositions for injection may be provided in the form of an ampule, each containing a unit dose amount, or in the form of a container containing multiple doses.

The saposin-C or prosaptide/toxin conjugate or signaling transduction pathway altering compound may be formulated into therapeutic compositions as pharmaceutically acceptable salts. These salts include the acid addition salts formed with inorganic acids such as, for example, hydrochloric or phosphoric acid, or organic acids such as acetic, oxalic, or tartaric acid, and the like. Salts also include those formed from inorganic bases such as, for example, sodium, potassium, ammonium, calcium or ferric hydroxides, and organic bases such as isopropylamine, trimethylamine, histidine, procaine and the like.

Controlled delivery may be achieved by admixing the active ingredient with appropriate macromolecules, for example, polyesters, polyamino acids, polyvinyl pyrrolidone, ethylenevinylacetate, methylcellulose, carboxymethylcellulose, prolamine sulfate, or lactide/glycolide copolymers. Altering the concentration of the macromolecules and/or the size of polymers may be used to control the rate of release of the active compound.

EXAMPLE 1

Materials and Cell Lines

Primary cultures of normal human prostate epithelial cells (NL.Pr.Ep; Catalogue No. CC-2655) and normal human prostate stromal cells (NL.Pr.St; Catalogue No. CC-2608) were purchased from BioWhittaker (Walkersville, Md.). The cells were maintained according to the manufacturer's instructions in a defined culture medium specific for each cell type, named "Pr.EGM" (Catalogue No. CC-3166) and "SCGM" (Catalogue No. CC-3205) for prostate epithelial and stromal cell lines, respectively. Other cell lines were obtained from the American Type Culture Collection (Manassas, Va.) and grown in the recommended media. For example, a neuroblastoma cell line (SK-N-MC; ATCC # HTB-10) that was known to respond to prosaposin (and Saposin C or TX14A) was purchased to use as a control. SK-NC-MC cells were grown in Eagle's Minimum Essential Medium (EMEM), 10% Fetal Bovine Serum (FBS), and 1.0 mM sodium pyruvate. This cell line was used as an external positive control for expression of prosaposin. Three human prostate cancer cell lines were purchased from the ATCC: PC-3 (ATCC # CRL-1435), DU-145 (ATCC # HTB-81), and LNCaP (ATCC # CRL-1740). The first two, PC-3 and DU-145, are androgen-insensitive cells lines, while LNCaP is an androgen-sensitive cell line. PC-3 and DU-145 were grown in DMEM with 10% FBS. LNCaP cells were grown in RPMI-1640/10% FBS, supplemented with 1 mM Na Pyruvate and 10 mM HEPES. In addition, a rat pheochromocytomal cell line (PC-12; ATCC No. CRL-1721) was purchased. PC-12 is also known to be responsive to both prosaposin and TX14A.

Human breast (MCF-7; ATCC # HTB-22), colon (LoVo; ATCC #CCL-229), and lung cancer (H1299; ATCC #CRL-5803) cell lines were purchased from American Type Culture Collection (Manassas, Va.). MCF-7 and H1299 cells were cultured in DMEM supplemented with 10% FBS. LoVo cells were cultured in Ham/F12 medium supplemented with 2 mM L-glutamine, 1.5 g/L sodium bicarbonate, and 10% FBS.

Human saposin C (Sap. C), goat anti-human saposin C, and goat anti-human saposin-D were obtained from Professor K. Sandoff (Bonn, Germany) and were previously characterized by ELISA, immunoblot, and immunoprecipitation as described in M. Hensler et al., "Expression of the three alternative forms of the sphingolipid activator protein precursor in baby hamster kidney cells and functional assays in a cell culture system," J. Biol. Chem., vol. 271, pp. 8416–8423 (1996). Rabbit anti-mouse prosaposin was a gift from Dr. Carlos Morales (McGill University, Montreal, Canada) and was previously characterized by immunohistochemical staining as described in M. Morales et al., "Targeted disruption of the mouse prosaposin gene affects the development of the prostate gland and other male reproductive organs," J. Androl., vol. 21, pp. 765–775 (2000).

TX14A, a peptide of 14 amino acids derived from the active neurotrophic region of saposin C, was synthesized commercially to 98% purity and purchased from AnaSpec (San Jose, Calif.). To assay for the intracellular kinase pathway, a Phospho-ERK1/2 pathway sampler kit and an anti-p42/44 antibody were purchased from Cell Signaling Technologies, Inc (Beverly, Mass.).

EXAMPLE 2

Expression of Saposin C and Prosaposin in a Neuroblastoma and Various Prostatic Cell Lines.

To assay for the expression of saposin C and prosaposin in a neuroblastoma cell line (SK-N-MC) and various prostatic cell lines (LNCaP, PC-3, DU-145, NL.Pr.St, and NL.Pr.Ep.), subconfluent culture plates were incubated for 24 h in a serum-free media that was specific for each cell line as described above. The media above the growing cells was collected ("Supernatant") and centrifuged at 2000×g for 10 min. Whole cells were collected and lysed in RIPA buffer (25 mM Tris, pH 7.5, 150 mM NaCl, 1% Nonident p-40, 0.5% sodium deoxycholate, 1% SDS, 10 mM sodium fluoride, and 1 mM sodium orthovandate) supplemented with protease inhibitors. The lysate was centrifuged at 2000×g for 10 min, and the clear supernatant collected ("Cell Lysate"). The protein concentration in the Supernatant and the Cell Lysate was measured by a BCA protein assay kit (Pierce, Rockford, Ill.). Ten μg Cell Lysate and 20 μg Supernatant were used for Western Blot analysis under reducing conditions according to the procedure described in S. Koochekpour et al., "The von Hippel-Lindau tumor suppressor gene inhibits hepatocyte growth factor/scatter factor-induced invasion and branching morphogenesis in renal carcinoma cells," Mol. Cell. Biol., vol. 19, pp. 5902–5912 (1999). Saposin C and prosaposin bands were identified using goat-anti-human saposin C as primary antibody and anti-goat-HRP (horse radish peroxidase; Catalogue No. SC-2033; Santa Cruz Biotechnology, Santa Cruz, Calif.) as secondary antibody, and were detected using a ECL (ElectroChemiLuminesence) detection system (Amersham, Piscataway, N.J.). SK-N-MC cells were used as a positive control cell line.

As seen in FIG. 1, immuno-reactive doublet bands of 62 and 64 kDa, indicating the presence of prosaposin, were detected in both cell lysates and supernatants. In a parallel experiment using anti-prosaposin and/or anti-saposin D as primary antibody, the same doublet bands were found (data not shown). The presence of doublet bands of prosaposin (PSAP) has been reported in human secretory fluids and is hypothesized to represent isoforms due to differences in glycosylation. See A. Sano et al., "Sphingolipid hydrolase activator proteins and their precursors," Biochem. Biophys. Res. Comm., vol. 165, pp. 1191–1197 (1989).

Figure 1B:
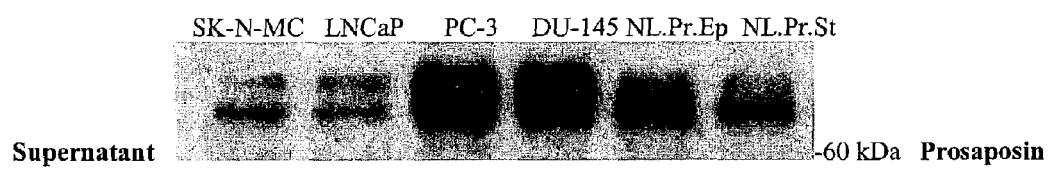
FIG. 1B illustrates the presence of prosaposin after secretion into the extracellular fluid by various cells lines, with the highest secretion level found in the two prostate cancer cell lines that are insensitive to androgen, PC-3 and DU-145.

In addition, as shown in FIG. 1A, a smaller band (about 10 kDa) was detected only in the Cell Lysate, and only with the anti-saposin C or anti-prosaposin antibody, but not with the anti-saposin D antibody. This smaller band represents saposin C expression. Saposin C expression in androgen-sensitive LNCaP cells, and normal prostate epithelial and stromal cells was higher than the androgen-resistant prostate cancer cells (PC-3 and DU-145).

The expression level of secreted prosaposin in the Supernatant, however, was in reverse order to that seen in the Cell Lysate (FIG. 1B), indicating a higher secretion level of prosaposin by the androgen-insensitive prostate cancer cell lines, PC-3 and DU-145. As shown below in Example 4, these cancer cells have a higher level of response to saposin C, which is derived from prosaposin. These two cell lines are known to be very aggressive tumors, and we have now shown that the cells secrete a molecule that both induces cell proliferation, migration, and invasion and increases the spreading of the cancer.

EXAMPLE 3

Saposin C and TX14A Protect Prostate Cancer Cells from Apoptosis.

To test for the effects of saposin C and TX14A (the synthetic prosapeptide from saposin C) on apoptosis in prostate cancer cells, sodium selenium (NaSe) was used to induce apoptosis as reported in D.G. Menter et al., "Selenium effects on prostate cell growth," Cancer Epidemiology, Biomarkers & Prevention, vol. 9, pp. 1171–1182 (2000). Cells were cultured in their respective complete culture media as given in Example 1 for two days. Cells were then treated with one of the following: (1) NaSe (10 μM); (2) NaSe (10 μM)+Saposin C (0.1 nM); (3) NaSe (10 μM)+Saposin C(1 nM); (4) NaSe (10 μM)+Saposin C (10 μM); or (5) NaSe (10 μM)+TX14A (10 nM). After incubation for 48 h, the percent dead cells were assayed by the trypan blue exclusion method. In this assay, 0.4% trypan blue dye was mixed with an equal volume of cell suspension. The dye will cross the cell membranes of both living and dead cells, but only living cells can expel the dye. The number of living (unstained) and dead (darkly stained) cells were counted under a microscope using a hemocytometer. The results in FIG. 2 are presented as the percent dead cells and are the mean +/- standard error of the mean (SEM) for three duplicate experiments.

Figure 2:
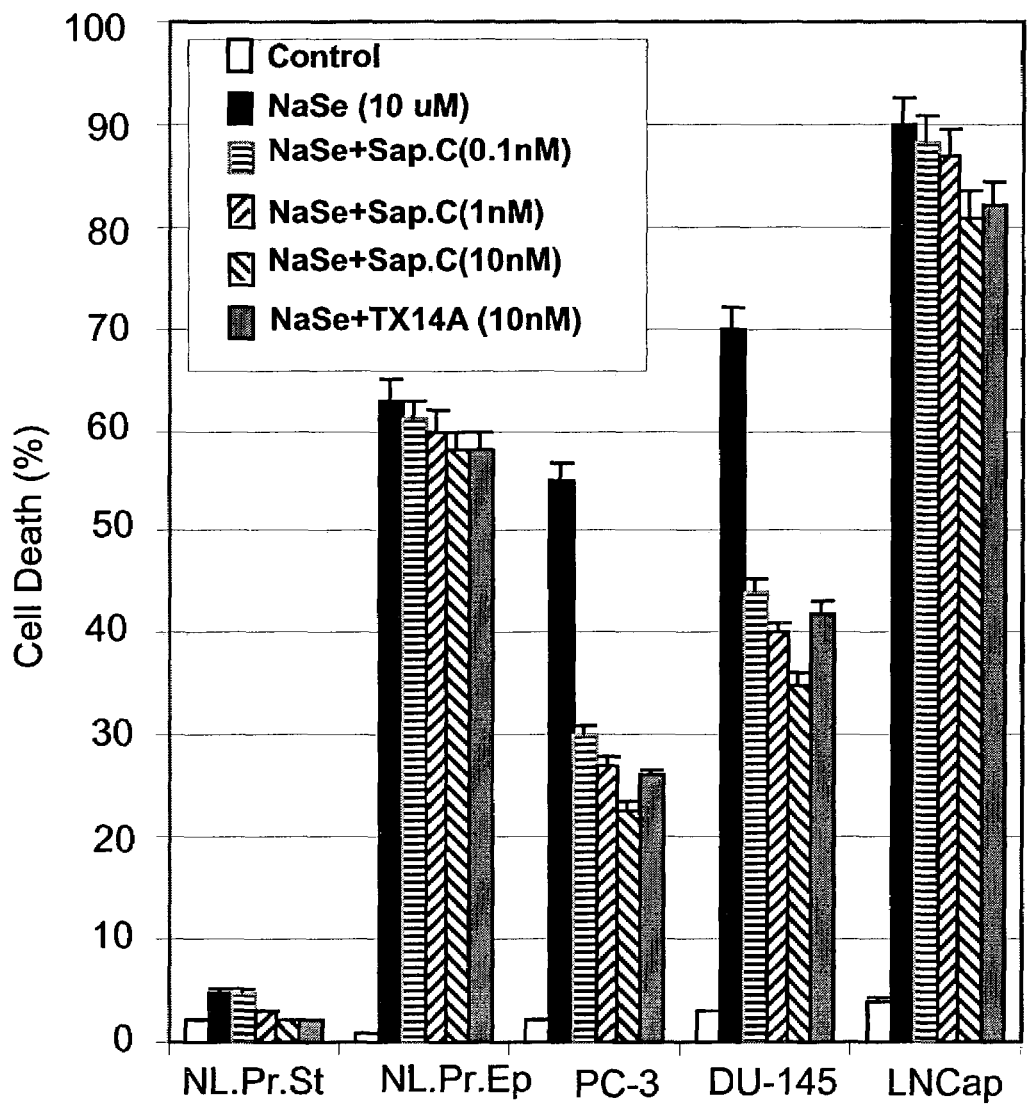
FIG. 2 illustrates the level of protection from cell death due to the presence of sodium selenium by applying various concentrations of saposin C and TX14A to various cell lines, with the highest effect seen in the two prostate cancer cell lines that are insensitive to androgen, PC-3 and DU-145.

As indicated in FIG. 2, normal prostate stromal cells were resistant to the toxic effect of NaSe. The rank order of overall survivability from lowest to highest in the presence of NaSe was LNCaP, DU-145, normal prostate epithelial cells, PC-3, and normal prostate stromal cells. The presence of saposin C in a dose dependent manner decreased the degree of cell death, indicating a protective and anti-apoptotic peptide-mediated effect. The extent of the protective effect, as expressed by the difference in the percent cell death with and without saposin C, was highest in PC-3 (55%) and DU-145 (50%). In addition, TX14A (at 10 nM), which mimics the tropic sequence of saposin C, was shown to be equally effective as saposin C (at 10 nM) in protecting cells from death in the presence of NaSe. Neither Saposin C nor TX14A protected normal prostate epithelial cells from cell death, and the protective effect on LNCaP was small (5–10%).

These results indicate that the greatest protection from apoptosis by saposin C was seen in the prostate cancer cell lines that are androgen-insensitive, PC-3 and DU-145. However, smaller but consistent effects were seen in the androgen-sensitive cells, e.g., LNCaP.

EXAMPLE 4

Effect of Saposin C and TX14A on Cell Proliferation.

To test the effects of saposin C and TX14A on cell proliferation, various cells were cultured as described in Example 1, incubated in only fresh media, or in media supplemented with saposin C or with TX14A at concentrations of 0.1, 1.0, and 10 nM. After incubation for 2 days, the number of living cells was determined by trypan blue exclusion method, as described above in Example 3. The results are shown in FIG. 3, in which each point represents the mean +/–SEM of three duplicate experiments.

Although saposin C did not show any effect on growth of normal prostate epithelial cells, both saposin C and TX14A stimulated cell proliferation in the other cell lines in a dose dependent manner. (FIG. 3) Expressed as a percent of the control values, the amount of proliferation in normal prostate stromal cells was 17–69%; in PC-3 cells, 20–53%; in DU-145 cells, 35–47%; and in LNCaP cells, 15–32%. Similar increases in cell number were obtained when the cells were counted using a Cell Proliferation Assay (Catalogue No. G5430) purchased from Promega (Madison, Wis.). (Data not shown).

Figure 3:
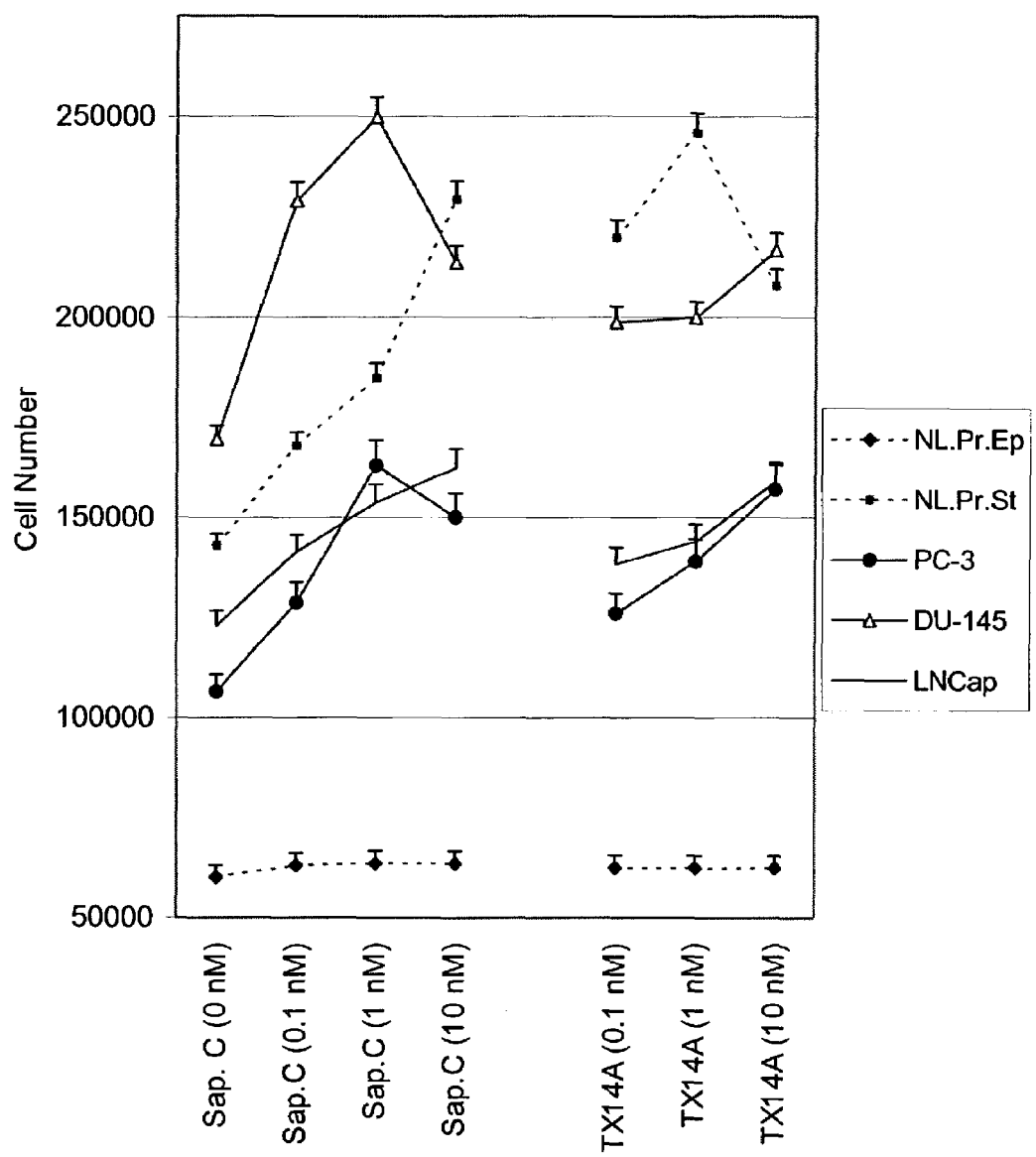
FIG. 3 illustrates the stimulation of cell proliferation by applying various concentrations of saposin C and TX14A to various cell lines, with the highest effect seen in the normal prostate stromal cell line and the prostate cell lines that are insensitive to androgen, i.e., Nl.Pr.St, PC-3, and DU-145.

The results shown in FIG. 2 and FIG. 3 indicate that saposin C and its trophic peptide (TX14A) has a greater effect on the androgen-insensitive cancer cell lines (PC-3 and DU-145) as measured by cell-death protection and promotion of cell proliferation (FIGS. 2 and 3, respectively). As noted in Example 3, smaller but consistent effects were seen in androgen-sensitive cells such as LNCaP. Prostate stromal cells were also stimulated to grow by Saposin C. Prostate stromal cells are thought to be critical in the development of prostate hyperplasia, and the effect of Saposin C on proliferation of these cells has therapeutic ramifications for benign prostate hyperplasia.

EXAMPLE 5

Effect of Saposin C on Migration and Invasion of Prostate Cells.

To test the effect of saposin C on prostatic cell migration and invasion, cell migration and invasion assays were performed using 24-well transwell units with 8-μm polycarbonate filters (Costar, purchased from Becton Dickinson, Bedford, Mass.), as described in S. Koochekpour et al., "Met and HGT/SF expression in human glioma," Cancer Res., vol. 57, pp. 5391–5398 (1997). For invasion assays, transwell filters were coated with 20 μg GFR-Matrigel matrix (Becton Dickenson) in 100 μl of basal medium, and left to air dry overnight. To the lower compartment of each transwell unit, was added 400 μl of basal media supplemented with 0.5% FBS and 0.1% BSA. Saposin C was then added to the lower compartment in the following concentrations: 0 (control), 0.1 nM, 1 nM, and 10 nM.

Figure 4A:
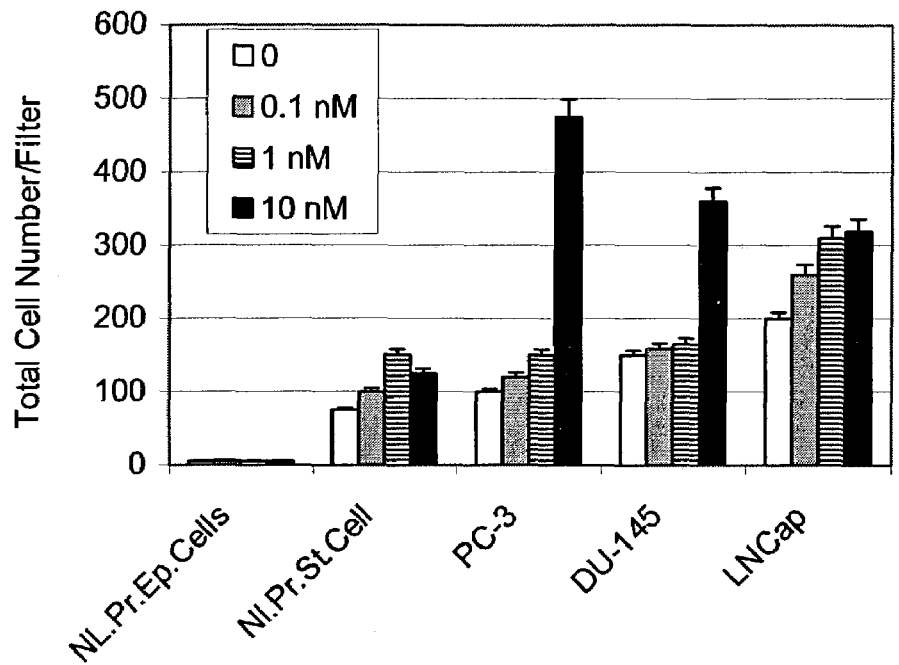
FIG. 4A illustrates the stimulation of cell migration by various concentrations of saposin C on prostate cell lines, indicating that the highest stimulatory effect was seen in the prostate cancer cell lines that are insensitive to androgen, i.e., PC-3 and DU-145.

Cultured cells were freshly harvested by trypsinization and counted. Approximately 5000 cells were resuspended in 100 μl of serum-free medium With 0.1% BSA, and were placed in the upper compartment of the transwell unit. After 16 h of incubation at 37° C., cells in both the upper and lower compartments were fixed in methanol and stained with Diff-Quick (Dade, Aguada, Puerto Rico). Non-migratory cells in the upper surface of the filter were removed by wiping with a cotton swab. Cells under the filter were counted. The results of cell migration are shown in FIG. 4A; and of cell invasion in FIG. 4B. Each bar represents the mean +/–SEM of three duplicate experiments, and samples from each experiment were counted at least three times.

Figure 4B:
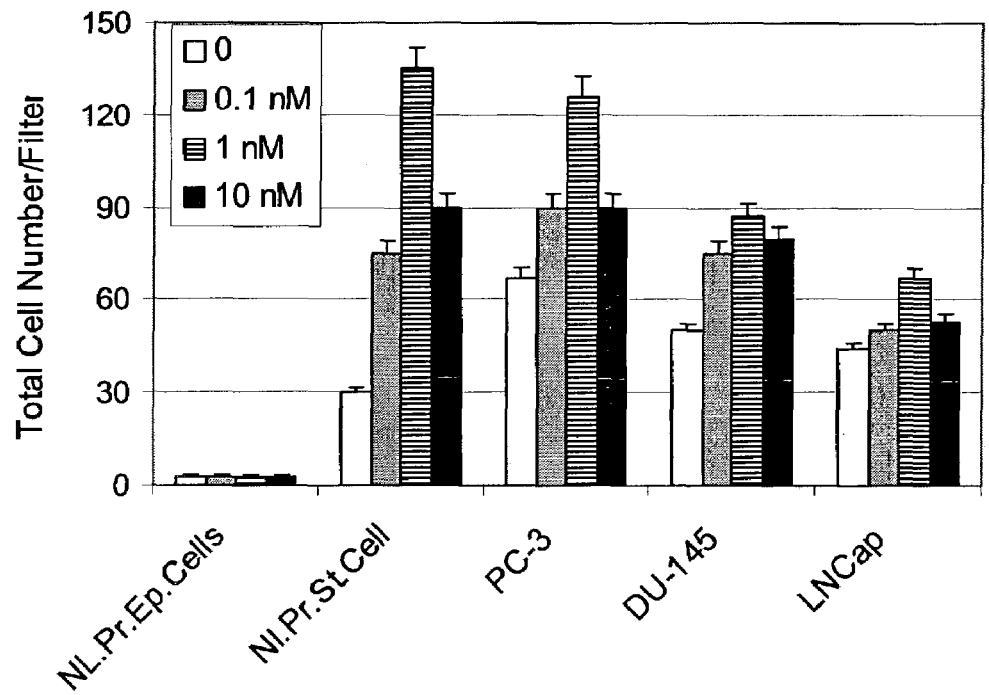
FIG. 4B illustrates the stimulation of cell invasion by various concentrations of saposin C on prostate cell lines, indicating that the highest stimulatory effect was seen in the normal prostate stromal cell line and in the prostate cell lines that are insensitive to androgen, i.e., PC-3 and DU-145.

As expected, normal primary prostate epithelial cells neither migrated through the filter nor invaded the Matrigel matrix either in the presence or absence of saposin C. (FIGS. 4A and 4B, NL.Pr.Ep.Cells). In the absence of saposin C, normal prostate stromal cells showed a lower level of cell migration and invasion than the prostatic cancer cells.

In the prostatic cancer cells, the rank order from lowest to highest of the increase in migration and invasion in response to saposin C was LNCaP, DU-145 and PC-3 (FIGS. 4A and 4B). Saposin C in a dose dependent manner stimulated migration in PC-3 by more than 300%, in DU-145 by 140%, and in LNCaP by 50%. In addition, saposin C stimulated invasion of PC-3 by 100%, DU-145 by 70%, and LNCaP cell by 48%. Thus, saposin C again had a greater effect on the androgen-insensitive cell lines, PC-3 and DU-145. Smaller, but consistent effects were again seen on the androgen-sensitive cell line, LNCaP. These findings, combined with the results in Example 2, indicate that both normal prostate stromal cells and cancer cells secrete and respond to saposin C by migration and invasion.

EXAMPLE 6

Effect of Androgens and Saposin C on Cathepsin D and Prosaposin Expression in Androgen-responsive Cells.

Lysosomal proteolysis of prosaposin by cathepsin D plays a major role in production of the mature saposins A, B, C, and D. Cathepsin D is a lysosomal aspartyl protease that is secreted as pro-cathepsin D and activated in an acidic environment, as occurs during tumor growth and invasion. Since saposin C stimulated migration and invasion of prostate cancer cells, experiments were designed to test whether the presence of saposin C or TX14A changed the expression level of cathepsin D.

Normal prostate stromal and cancerous LNCaP cells are known to be androgen-sensitive and to contain receptors for androgens. These cell lines were used to test the effect of androgens on expression of prosaposin and Cathepsin D. Cells were cultured in the preferred media (described in Example 1) up to 80% confluency. Tissue culture plates wee washed twice and pre-incubated in serum-free media for 2 h. After removing culture supernatent, the cells were washed twice with Phosphate Buffered Saline (PBS), and incubated in serum-free medium supplemented with the following concentrations of saposin C or TX14A: 0, 0.1, 1 and 10 nM. In a parallel experiment, the cells were treated with androgens, both testosterone (T) and dihydrotestosterone (DHT) (Cat# T-5035 and D-7149, respectively; Sigma Chemical Company, St. Louis, Mo.), at the following concentrations: 0, 0.1, 1, and 10 nM. At the end of 24 h, the cell-conditioned medium was collected, and centrifuged at 2000 g for 30 min at 4° C. The supernatants were concentrated 5-fold using a Centriprep-3 concentrator (Amikon, Beverley, Mass.), and then stored frozen in −70° C. until use.

Supernatants (15 µg/sample) were subjected to SDS-PAGE under reducing conditions, and the separated proteins were electroblotted onto PVDF membranes (Cat# RPN 2020F, Amersham, Piscataway, N.J.). A Western blot analysis was performed using commercially available anti-cathepsin D antibody (Cat# SC-6486, Santa Cruz Biotechnology, Santa Cruz.

Figure 5:
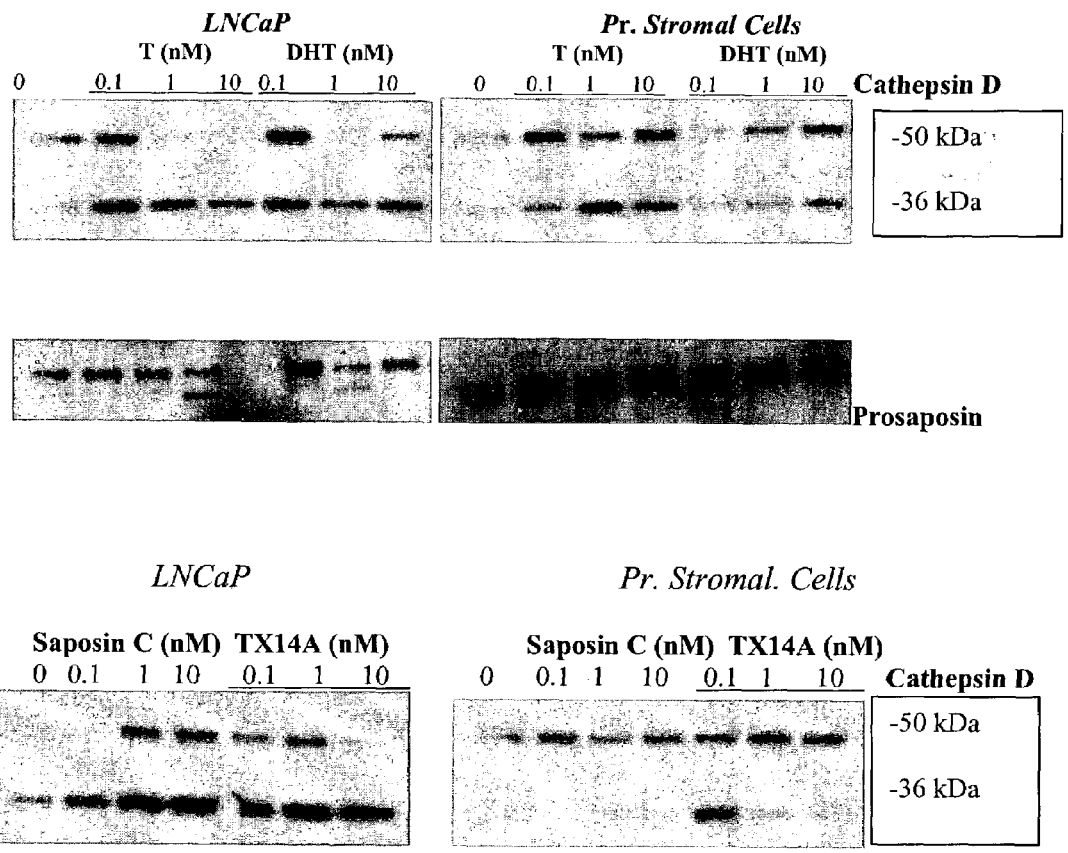
FIG. 5 illustrates the effect of androgens (testosterone (T) and dihydrotestosterone (DHT)), and of saposin C and TX14A on the expression of pro-cathepsin D (50 kDa bands) and Cathepsin D (36 kDa bands) and prosaposin in the culture supernatant of normal prostate stromal cells and a prostate cancer cell line, LNCaP.

The results are shown in FIG. 5. Compared to the control levels (0 nM), androgens, saposin C, and TX14A were all able to stimulate expression of pro-cathepsin D (the 50 kDa band) and the active mature cathepsin D (the 36 kDa band) in both LNCaP and normal prostate stromal cells. This result indicated that saposin C (prosaposin and TX14A) can function similar to androgens in androgen-sensitive normal prostate stromal and prostatic cancer cells (LNCaP), at least in stimulating the expression of pro-cathepsin and cathepsin D. The presence of both saposin C (or TX14A) and androgen (T or DHT) would greatly increase the expression of pro-cathepsin D and cathepsin D. Cathepsin D has been suggested to play an integral role in promoting growth and invasion of malignant tumors, including prostate cancer. See J. P. Cherry et al., "Analysis of cathepsin D forms and their clinical implications in prostate cancer," J. Urol., vol. 160, pp. 2223–2228 (1998). Thus the presence of androgens and saposin C may increase the malignancy of prostate cancer by increasing the cathepsin D levels.

Interestingly, both androgens (T and DHT) in this assay stimulated the expression of prosaposin in both LNCaP and normal prostate stromal cells. This finding indicated that androgens may be a factor in regulating the expression of prosaposin. This androgen-receptor activation not only provides more prosaposin to both tumor cells and stromal cells in a prostate tumor microenvironment, but also will increase the malignant phenotype of the prostate cancer through production of more prosaposin and cathepsin D.

EXAMPLE 7

Effect of Saposin C on Urokinase-Type Plasminogen Activator and its Cell Membrane Receptor To investigate the effect of saposin C on expression of both urokinase-type plasminogen activator (uPA) and the soluble uPA receptor (uPAR), normal prostate stromal cells and prostatic cancer cells (PC-3, DU-145, LNCaP) were cultured in media as described in Example 1. The cells were cultured in the preferred media up to 80% confluency, then washed twice with PBS, and incubated for 24 h at 37° C. in serum-free medium supplemented with either 0, 0.1, 1.0 or 10 nM saposin C. At the end of the incubation period, the cell-conditioned medium (Supernatant) was collected. The Supernatants were concentrated 5-fold using Centriprep-3 concentrator (Amikon, Beverley, Mass.), and stored frozen in −70° C. until use.

Supernatants (15 µg/sample) were subjected to SDS-PAGE under reducing conditions, and the separated proteins were electroblotted onto PVDF membranes (Cat# RPN 2020F, Amersham, Piscataway, N.J.). A Western blot analysis was performed (as in Examples 2 and 6) using commercially available anti-uPA and anti-uPAR antibodies (Cat# 389 and Cat# 399R, respectively; American Diagnostica Inc., Greenwich, Conn.).

Figure 6:
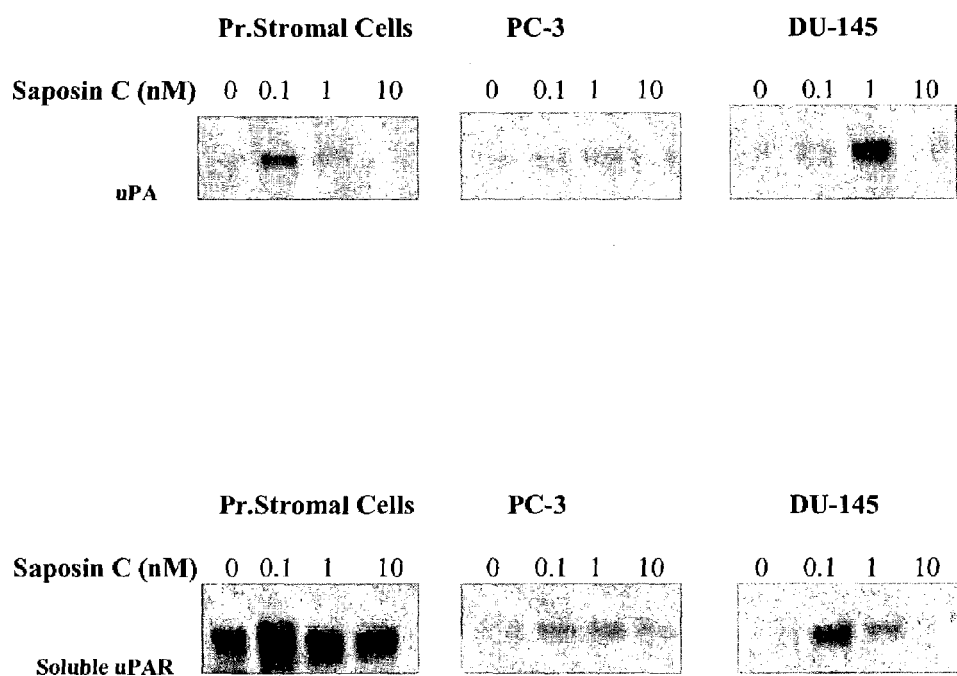
FIG. 6 illustrates the effect of Saposin C on urokinase-type plasminogen activator (uPA) and urokinase-type plasminogen activator receptor (uPAR) in normal prostate stromal cells and two androgen-insensitive cell lines, PC-3 and DU-145.

Under these experimental conditions, no expression of either uPA or soluble uPAR was detected in the supernatant from LNCaP cells. (Data not shown) In contrast, as shown in FIG. 6, PC-3, DU-145, and normal prostate stromal cells were positive for expression of uPA and uPAR. Saposin C increased the extracellular level of both uPA and uPAR in stromal cells as well as in the prostatic cancer cells (PC-3 and DU-145). The increase of both uPA and uPAR levels indicates an additional mechanism by which saposin C might increase the migration and invasion of prostatic cancer cells that are insensitive to androgens. Furthermore, these results support a potential role for saposin C as a mediator of tumor-cell-stromal interaction in cancer invasion and metastasis. The normal prostate stromal cells secrete and increase the extracellular level of uPA and soluble uPAR to the microenvironment of the tumor cells.

EXAMPLE 8

Effect of Saposin C and TX14A on PSA Expression in LNCaP Cells

LNCaP is an androgen-sensitive cell line, which has been shown to be sensitive to both androgens and anti-androgens. To investigate the effect of saposin C on the expression of PSA in LNCaP cells, cells were cultured in the preferred media up to 80% confluency, and then washed twice with PBS. The cells were incubated in serum-free medium supplemented with either testosterone (T), dihydrotestosterone (DHT), saposin C or TX14A at the following concentrations: 0, 0.1, 1 or 10 nM. At the end of 24 h, the cell-conditioned medium was collected. The supernatants were concentrated 5-fold using Centriprep-3 concentrator (Amikon, Beverley, Mass.) and stored frozen in −70° C. until use. A Western blot analysis was performed (as in Examples 2 and 6) using commercially available anti-PSA (Santa Cruz Biotechnology, Santa Cruz, Calif.).

Figure 7:
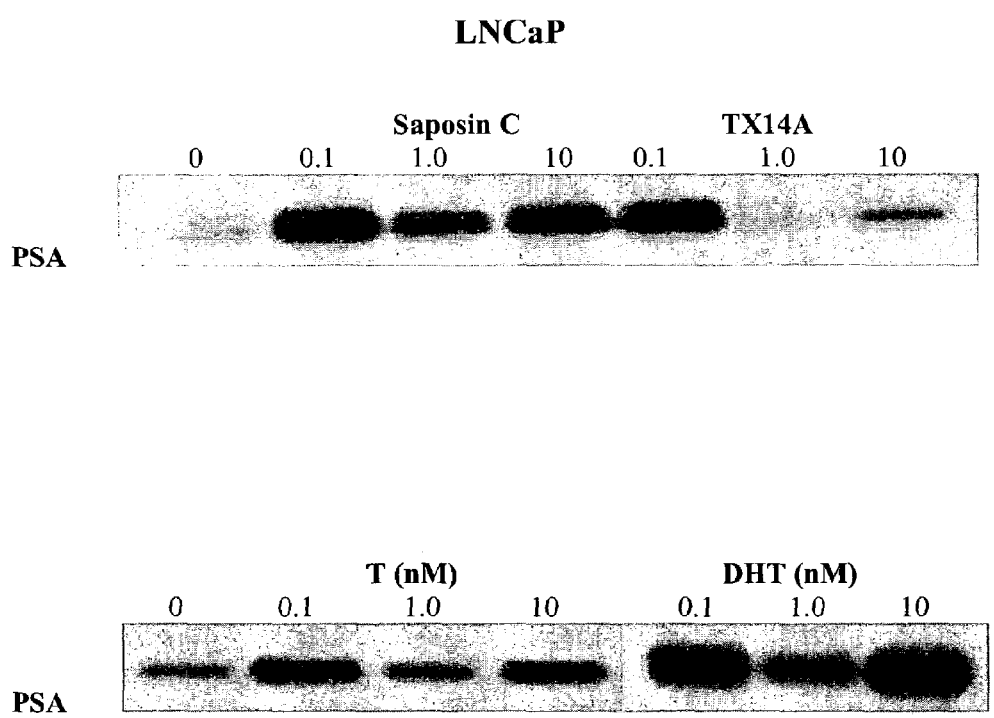
FIG. 7 illustrates the effect of Saposin C, TX14A, and androgens (T and DHT) on prostate specific antigen (PSA) expression in the androgen-sensitive prostate cancer cell line, LNCaP.

The results are shown in FIG. 7. Similar to the known effect of androgens (testosterone and dihydrotestosterone) (bottom panel), both saposin C and TX14A significantly increased the extracellular level of PSA at concentrations as low as 0.1 nM (top panel). This result demonstrates for the first time that saposin C (or its synthetic peptide) is a strong regulatory molecule for the expression of androgen-responsive gene (PSA). Saposin C may provide cellular signals that interact through the androgen receptor to mediate androgen-like actions. Thus saposin C may mediate development of androgen-independent phenotype in prostate cancer.

EXAMPLE 9

Activation of MEK1/2-ERK1/2-RSK Signaling Transduction Pathway by Saposin C and TX14A.

Experiments were designed to test the effect of saposin C and TX14A on the MAPK pathway in normal prostate epithelial and stromal cells and in the prostate cancer cells, PC-3, DU-145, and LNCaP.

Cells were grown to 80% confluency by incubating in their respective serum-free basal media for 18 h. For each cell line, tissue culture plates were pre-treated with a specific MEK1/2 inhibitor (U0126, Cat.# 9903, Cell Signaling Technology, Beverly, Mass.) at 10 μM for 1.5 h. Saposin C and TX14A were added at the following concentrations: 0.1, 1.0, and 10 nM. The cells were then incubated at 37° C. for 5 min, washed, and lysed on ice in RIPA buffer supplemented with protease inhibitors and 1 mM sodium orthovandate, as described in S. Koochekpour et al., 1999. Clarified cell lysates were subjected to Western analysis using phospho-specific antibodies against three enzymes in the MAPK Pathway: MEK1/2 (Ser217/22; Cat.# 9121; Cell Signaling Technology, Beverly, Mass.); p90RSK ($p90^{rsk}$, Ser380, Cat# 9341, Cell Signaling Technology); and p42/44 MAP Kinases ($p44^{MAPK}$, $p42^{MAPK}$; Thr202/Tyr204, Cat# 9102; Cell Signaling Technology). Primary antibodies against p42/44 MAP kinase (Cell Signaling Technology) or against tubulin (Cat# 12463, Santa Cruz Biotechnology, Santa Cruz, Calif.) were used as controls. To quantify the difference between the control and the various treatments, the autoradiograms were read on a densitometer, an Alpha Imager 2000 (Alpha Innotech Corp., San Leandro, Calif.).

Figure 8:
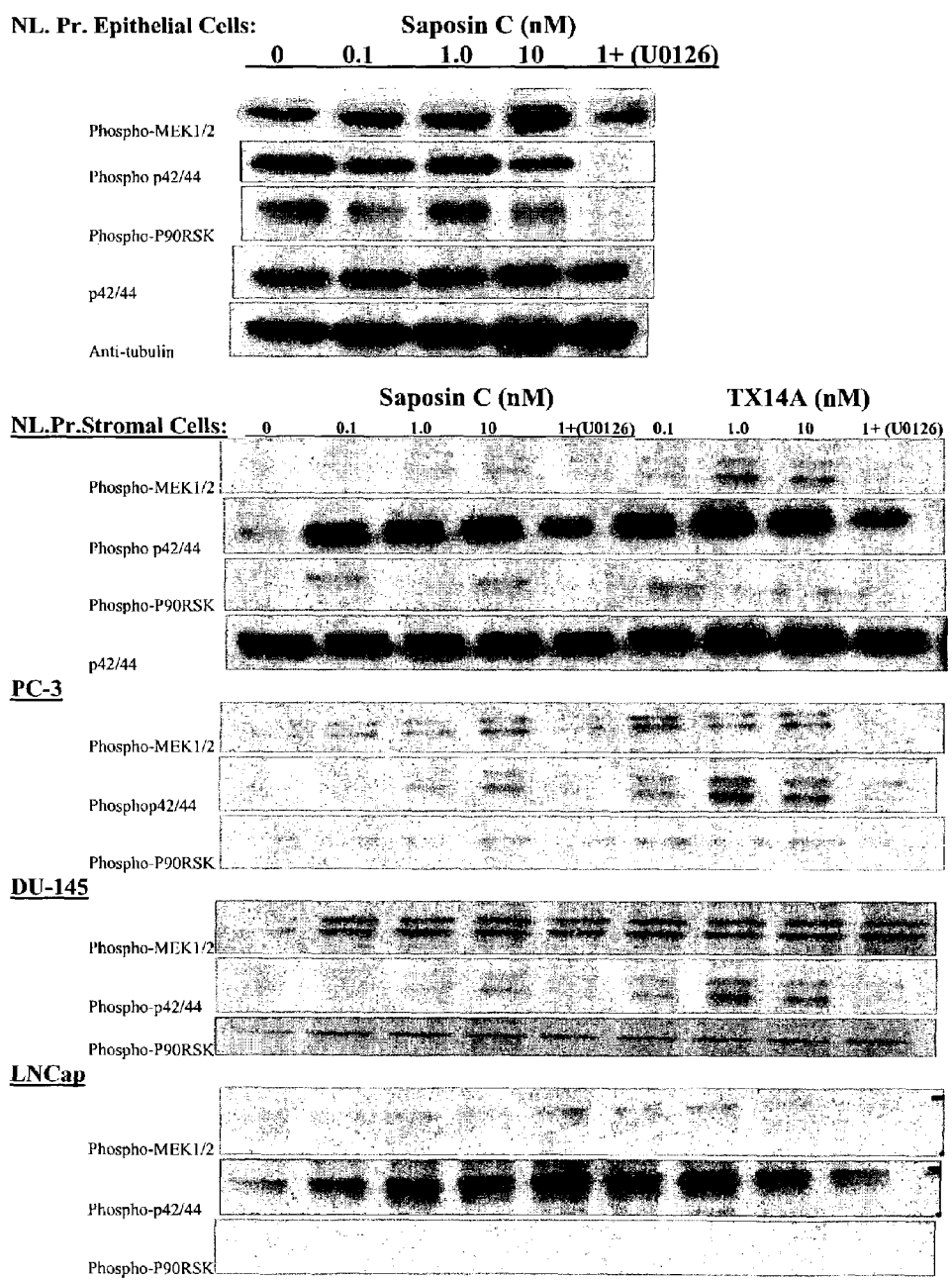
FIG. 8 illustrates the effect of saposin C and TX14A on the phosphorylation of certain enzymes in the intracellular MAPK signaling pathway, indicating an increase in phosphorylation in normal prostate epithelial and stromal cells as well as prostate cancer cell lines (PC-3, DU-145, and LNCaP).

As shown in FIG. 8, both saposin C and its active peptide (TX14A) at nanomolar concentrations activated the enzymes in the MAPK signaling transduction pathway in normal prostate stromal cells (NLPr Stromal Cells) and in the prostate cancer cells, PC-3, DU-145, and LNCaP. In these cell types, this activation was substantially inhibited by the MEK1/2 inhibitor, U0126. In normal prostate stromal cells, a 15-fold increase as compared to the control, was seen in p42/44 phosphorylation in response to saposin C and TX14A. For both stromal cells and PC-3 cells, a 1 to 5 fold increase in the level of phosphorylation for p90RSK proteins was found.

As shown in FIG. 8, both saposin C and TX14 were able to induce phosphorylation of the two isoforms of ERK (p42/44) and MEK almost equally, in the prostate stromal cells and cancer cells. The response of normal prostate epithelial cells to saposin C was different than any other cells in this study. Although a dose-dependent increase in the expression of MEK1/2 was found, a unique biphasic pattern for the enzymes, p42/44 and p90RSK, was seen. When compared to control values, the phosphorylation activity decreased at 0.1 nM, increased at 1.0 nM, and decreased at 10 nM (FIG. 8). This biphasic pattern was also seen for p90RSK activity in normal prostate stromal cells in response to both saposin C and TX14A. This bimodal response to saposin C and TX14A may be due to enhanced down modulation of receptor(s) or enhanced phosphatase activity.

Using the same experimental conditions above and a Biotrak in vitro p42/44 kinase assay (Amersham Life Sciences, Buckinghamshire, England), the incorporation of [γ-32P]ATP into a specific synthetic peptide was measured at 30° C. for a period of 30 minutes, as described in W. M. Campana et al., "Induction of MAPK phosphorylation by prosaposin and prosaptide in PC12 cells," Biochem. Biophys. Res. Comm., vol. 229, pp. 706–712 (1996). The synthetic peptide of the assay is more specific for p42/44 MAPK than the more commonly used substrate (MBP). The data verified the pattern of activation and phosphorylation by Saposin C and TX14A as reported above (data not shown). As an external positive control cell line, PC12 cells (pheochromocytoma) incubated with either 20% FBS, saposin C, or TX14A were used.

EXAMPLE 10

Expression of Saposin C and Prosaposin in Non-Prostatic Cancer Cell Lines.

To assay for the expression of saposin C and prosaposin in additional cancer cell lines, human breast cancer cell line (MCF-7), colon cancer cell line (LoVo), and lung cancer cell line (H1299) were incubated in subconfluent culture plates and samples collected as described above in Example 2. The samples were then assayed using a Western analysis under reducing conditions as described in Example 2.

Figure 9A:
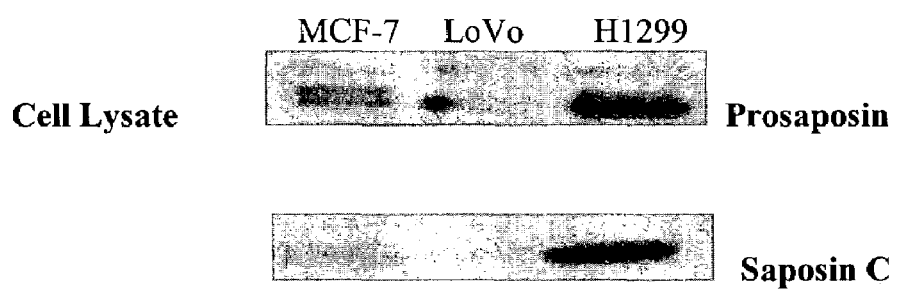
FIG. 9A illustrates the presence of prosaposin and saposin C in the intracellular fluid extracted from various non-prostatic cancer cell lines (lung cancer, H1299; colon cancer, LoVo; and breast cancer, MCF-7).
Figure 9B:
FIG. 9B illustrates the presence of prosaposin after secretion into the extracellular fluid by various non-prostatic cancer cell lines (lung cancer, H1299; colon cancer, LoVo; and breast cancer, MCF-7).

As shown in FIG. 9, prosaposin was detected both in the Supernatant and Cell Lysate of all three cancer cell lines. The expression of prosaposin was highest in lung carcinoma cells (H1299), and lowest in colon carcinoma cells (LoVo). Saposin C was detected in the Cell Lysate of all three cell types. The order from highest to lowest was the same as seen for prosaposin expression, i.e., lung carcinoma, breast carcinoma, and colon carcinoma.

Thus these non-prostatic cancer cell lines were also found to express prosaposin and saposin C.

EXAMPLE 11

Effect of Saposin C on Cell Migration and Invasion of Non-Prostatic Cancer Cell Lines To test the effect of saposin C on migration and invasion of non-prostatic cancer cells, assays using human breast cancer cell line (MCF-7), colon cancer cell line (LoVo), and lung cancer cell line (H1299) were performed in 24-well transwell units with polycarbonate filters as described above in Example 5.

Figure 10:
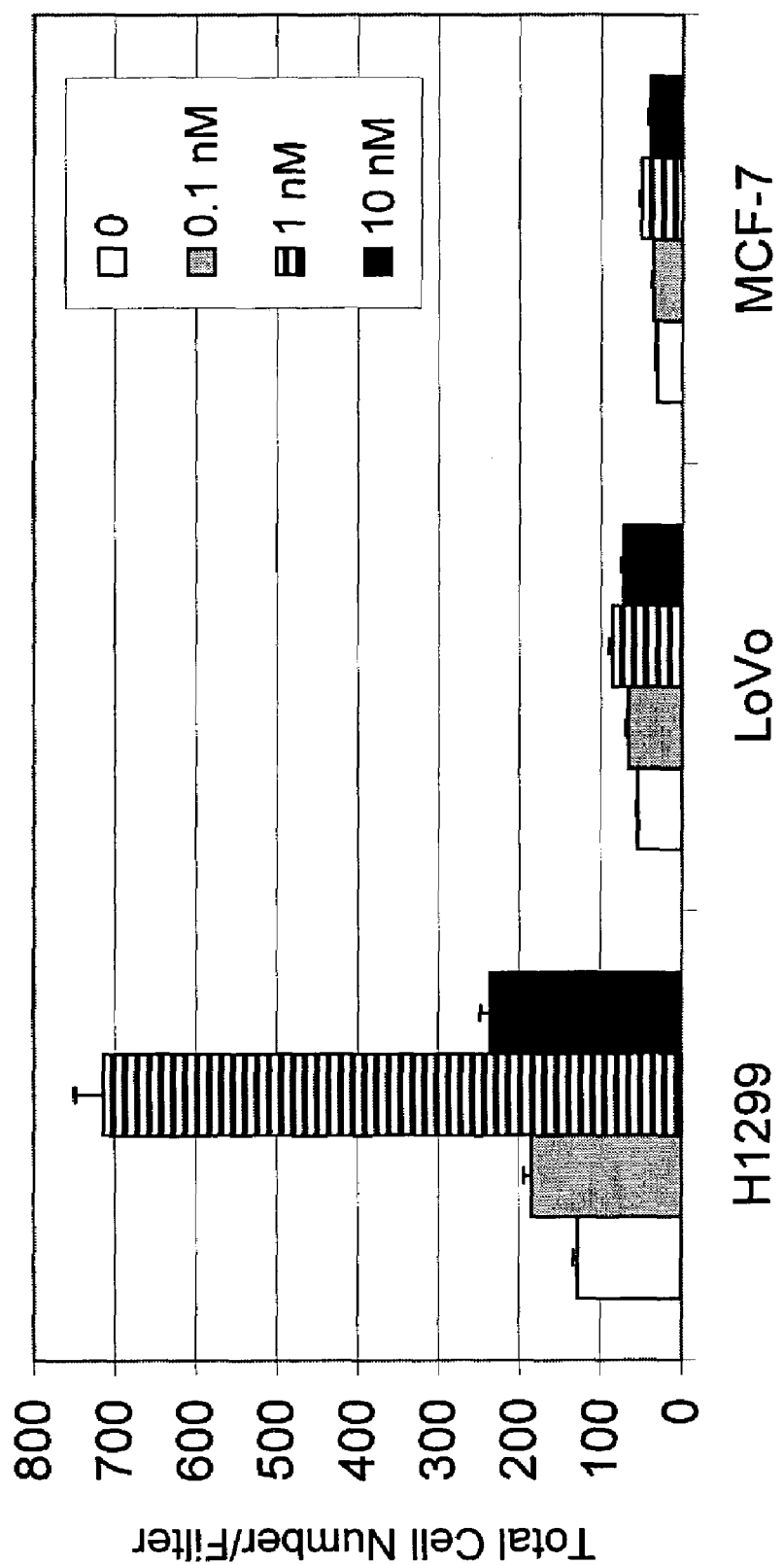
FIG. 10 illustrates the stimulation of cell migration by various concentrations of saposin C on various non-prostatic cancer cell lines (lung cancer, H1299; colon cancer, LoVo; and breast cancer, MCF-7).
Figure 11:
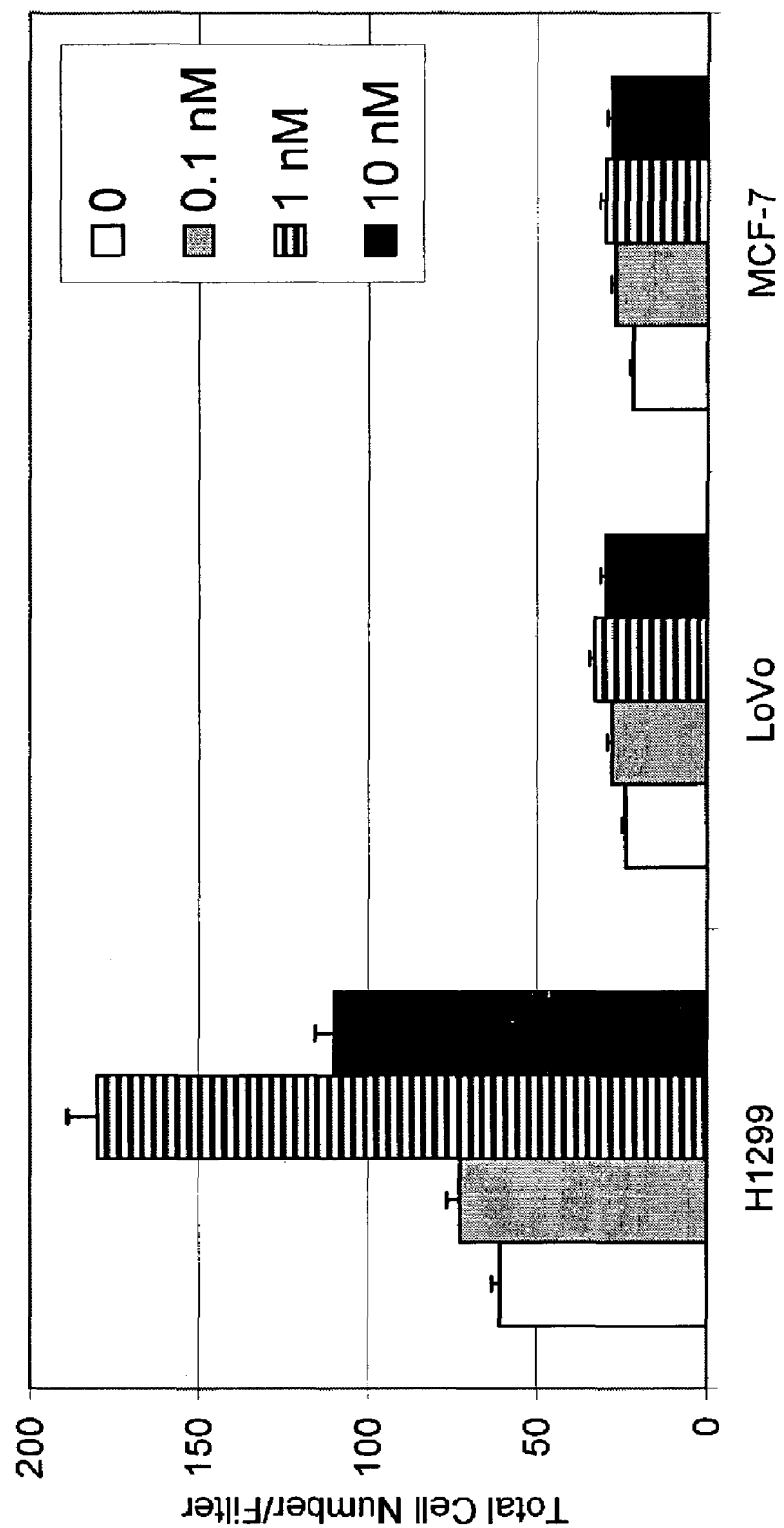
FIG. 11 illustrates the stimulation of cell invasion by various concentrations of saposin C on various non-prostatic cancer cell lines (lung cancer, H1299; colon cancer, LoVo; and breast cancer, MCF-7).
Figure 12:
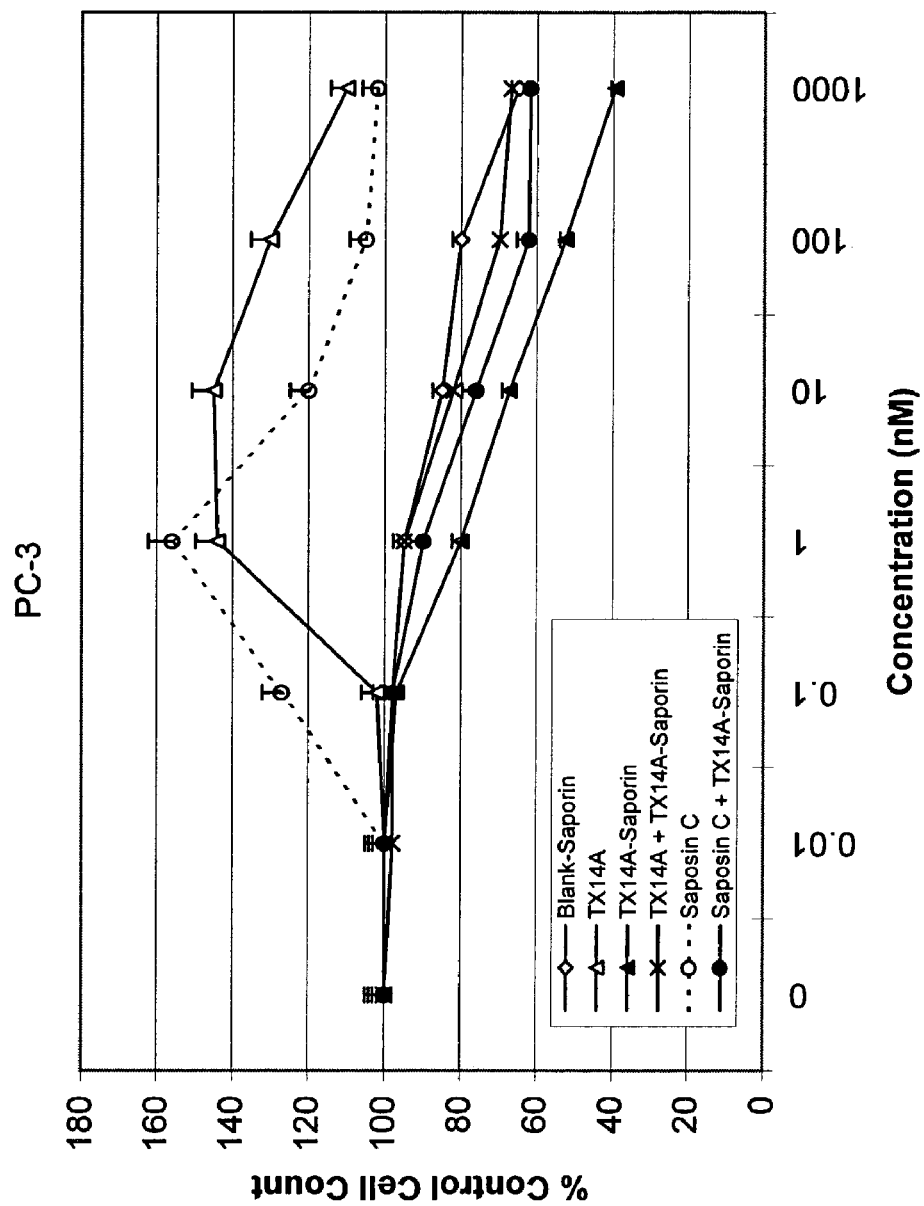
FIG. 12 illustrates the effect on number of androgen-insensitive, prostate cancer (PC-3) cells of various concentrations of TX14A, saposin C, a TX14A-saporin conjugate, a blank-saporin conjugate, a mixture of TX14A and the TX14A-saporin conjugate, and a mixture of saposin C and the TX14A-saporin conjugate.
Figure 13:
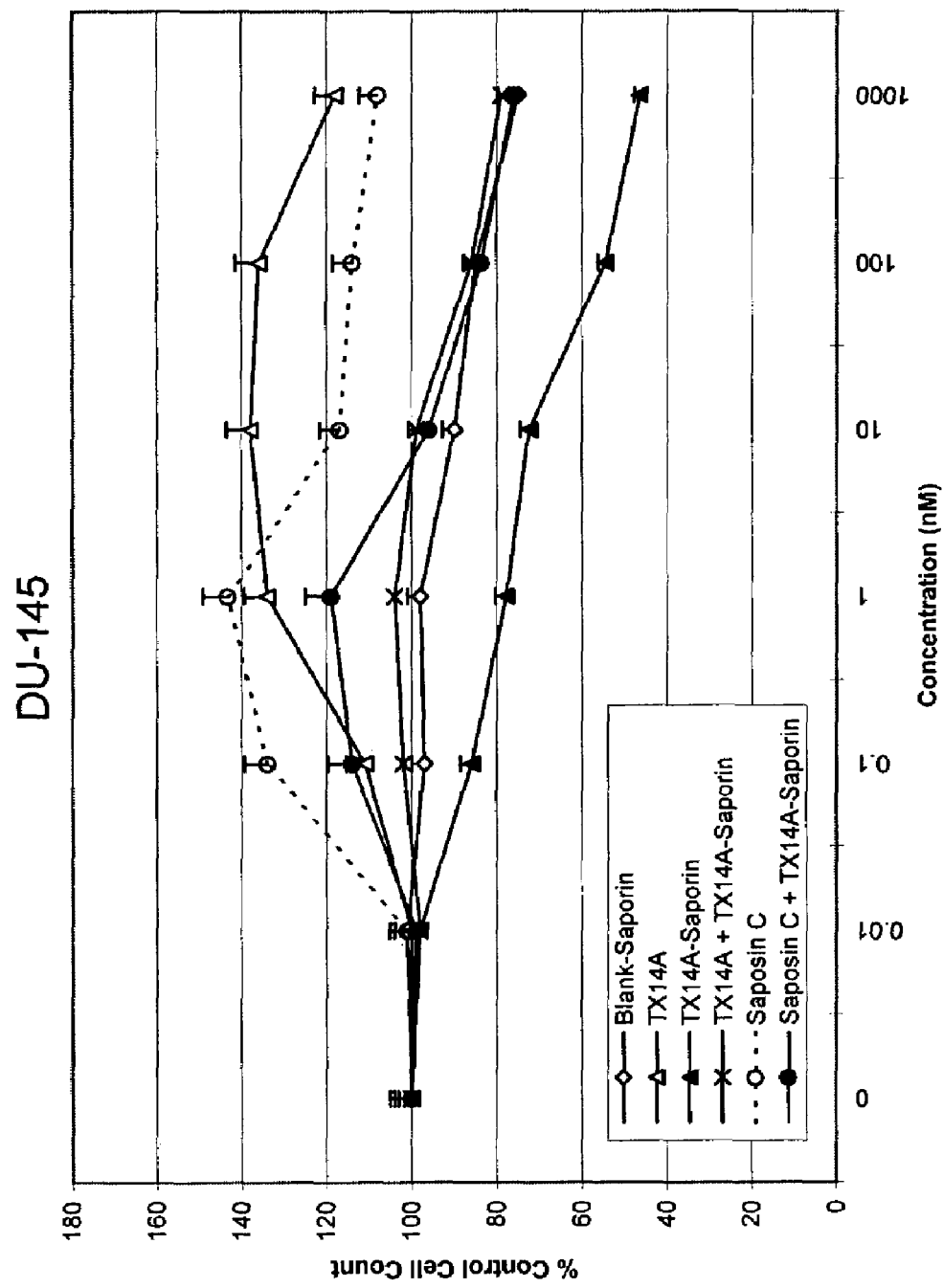
FIG. 13 illustrates the effect on number of androgen-insensitive prostate cancer (DU-145) cells of various concentrations of TX14A, saposin C, a TX14A-saporin conjugate, a blank-saporin conjugate, a mixture of TX14A and the TX14A-saporin conjugate, and a mixture of saposin C and the TX14A-saporin conjugate.
Figure 14:
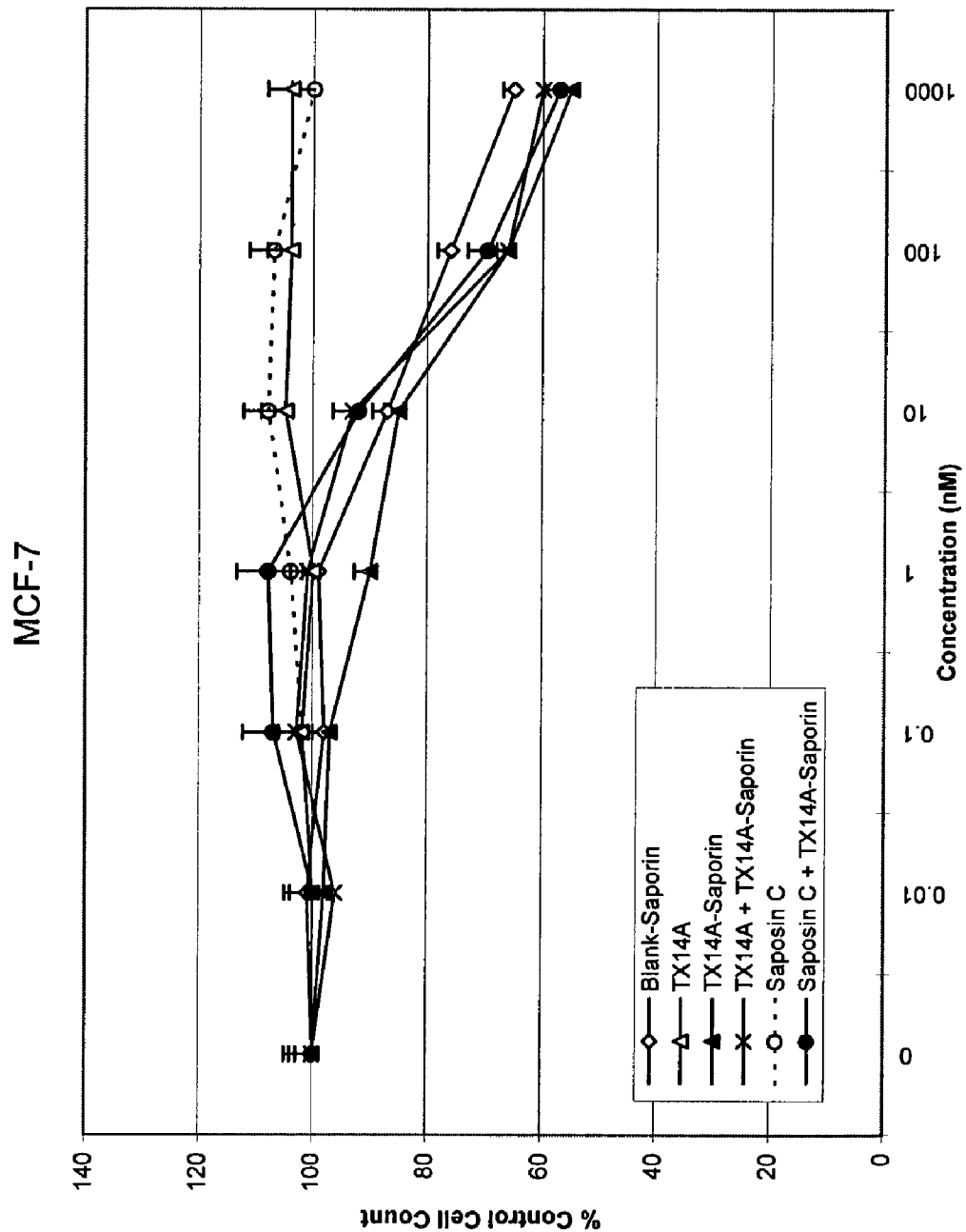
FIG. 14 illustrates the effect on number of breast cancer (MCF-7) cells of various concentrations of TX14A, saposin C, a TX14A-saporin conjugate, a blank-saporin conjugate, a mixture of TX14A and the TX14A-saporin conjugate, and a mixture of saposin C and the TX14A-saporin conjugate.
Figure 15:
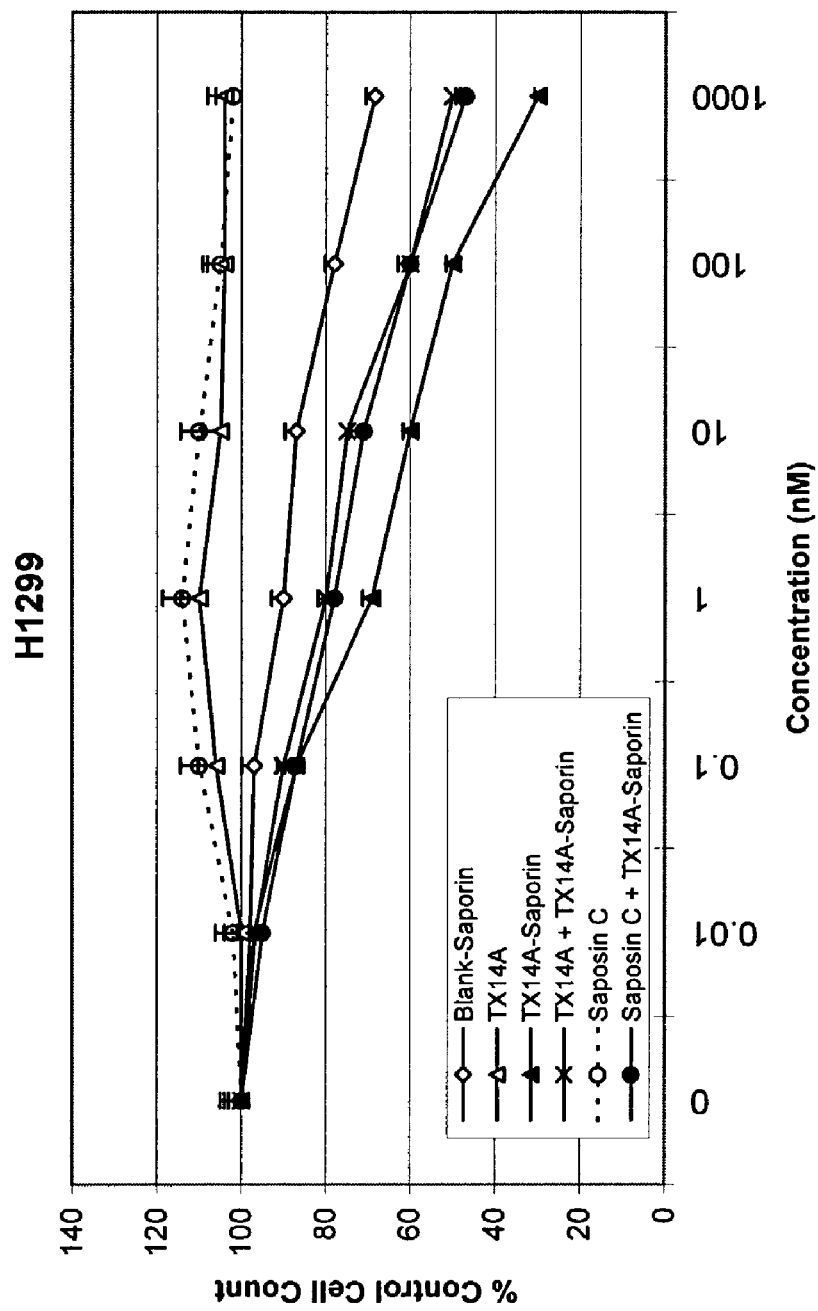
FIG. 15 illustrates the effect on number of lung cancer (H1299) cells of various concentrations of TX14A, saposin C, a TX14A-saporin conjugate, a blank-saporin conjugate, a mixture of TX14A and the TX14A-saporin conjugate, and a mixture of saposin C and the TX14A-saporin conjugate.

The results are shown in FIGS. 10 and 11. In the absence of saposin C, the lung carcinoma cells (H1299) displayed higher migration and invasion properties than either the breast or colon cancer cells. Saposin C stimulated the migration and invasion of all three cancer cell lines. Migration was increased by saposin C in the following order, highest to lowest effect: lung cancer cells (H1299), 44–460%; colon cancer cells (LoVo), 22–59%; and breast cancer cells (MCF-7), 12–59%. (FIG. 10). Invasion was increased by saposin C in the following order, highest to lowest: lung cancer cells, 19–195%; colon cancer cells, 16–37%; and breast cancer cells, 22–36%. (FIG. 11) For all cells tested, the highest migration and invasion was seen at a concentration of 1 nM saposin C, levels which are readily detectable in human body fluids (e.g., prostatic secretion, seminal plasma, blood, etc.).

These results coupled with the results of Example 5 on prostatic cancer cells indicate that the stimulatory effect on migration and invasion by saposin C is not limited to prostate cancer but extends to a wide variety of cancer cells, e.g., malignantly transformed epithelial cells.

EXAMPLE 12

Effect of Conjugated TX14A-Saporin on Various Cancer Cell Lines

In all the assays performed in this study, saposin C acted as a multipotential growth factor. Because of the considerable similarity of the biological effects of TX14A (trophic peptide derived from Saposin C) and saposin C, we decided to use a conjugate of TX14A and a toxin (saporin: from a plant called *Saponaria Officinalis*) and to test its anti-tumor activity (cell-killing) on prostate (PC-3, DU-145, LNCaP), breast (MCF-7), lung (H1299), and colon (LoVo) cancer cells. These cells were chosen because of the demonstrated Saposin C mediated cellular effects noted in the above examples.

The conjugate of saporin and TX14A was made by special order by Advanced Targeting Systems with a 1:1 molar ratio between the peptide and saporin. Blank-SAP, a non-targeted saporin conjugate, was purchased as a control (ATS, Catalogue# IT-21). Exponentially growing cells were trypsinized and cultured in their complete culture media (1000/well in 96-well plates) as described in Example 1. After 1 day of incubation at 37° C., the culture media were supplemented with either TX14A, saporin, TX14A-saporin (conjugate), Saposin C, TX14A-saporin plus TX14A, or TX14A-Saporin plus Saposin C at the following concentrations: 0, 0.1, 1, 10, 100, 1000 nM. Three days after treatment, cell death was monitored with a Promega (Madison, Wis.) cell titer cytotoxicity kit. Cell counts were normalized to the media controls.

The results for the cell lines of PC-3, DU-145, MCF-7, H1299, and LoVo are shown in FIGS. 12, 13, 14, 15, and 16, respectively. Although cell proliferation of all cancer cell lines was increased by either saposin C or TX14A, the effect was again much greater in the prostatic cancer cell lines, PC-3 and DU-145.

Figure 16:
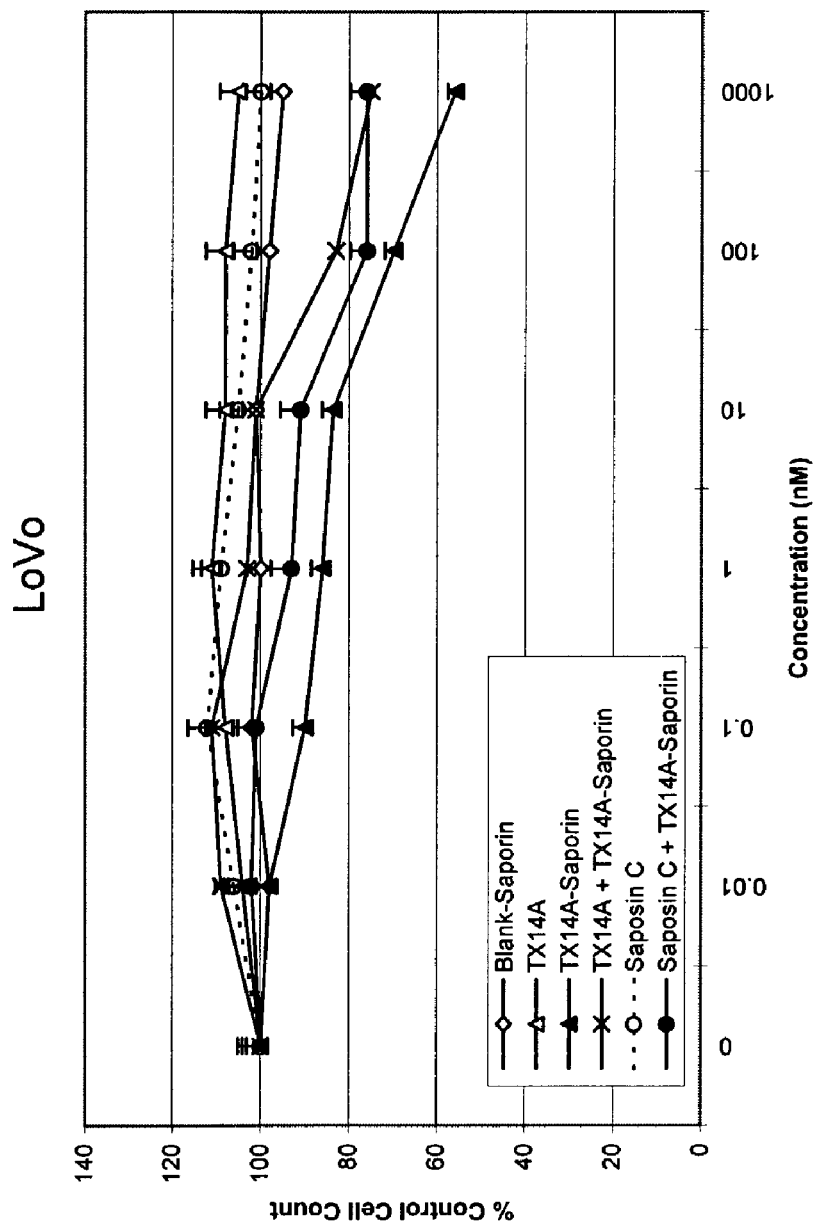
FIG. 16 illustrates the effect on number of colon cancer (LoVo) cells of various concentrations of TX14A, saposin C, a TX14A-saporin conjugate, a blank-saporin conjugate, a mixture of TX14A and the TX14A-saporin conjugate, and a mixture of saposin C and the TX14A-saporin conjugate.

TX14A-saporin conjugate at a concentration between 1 to 100 nM was found to inhibit cell proliferation in all tested cell lines: a decrease of 20–38% in PC-3 (FIG. 12), 23–46% in DU-145 (FIG. 13), 31–50% in H1299 cells (FIG. 14), 14–30% in LoVo (FIG. 15), and 10–34% in MCF-7 cells (FIG. 16). TX14A-Saporin demonstrated minimal cytotoxic effect in prostate stromal and LNCaP cells (Data not shown). The rank order of overall cytotoxic (cell-killing) effect of TX14A-saporin of cells from highest to lowest was H1299, DU-145, PC-3, MCF-7, LoVo, LNCaP, and normal prostate stromal cells.

In competitive inhibition assays (treating cells simultaneously with equimolar mixture of TX14A-saporin and TX14A or Saposin C), TX14A-saporin cytotoxicity was inhibited in a dose dependent manner by either TX14A or Saposin C (FIGS. 12–16). Blank-saporin (a non-specific saporin control molecule) cytotoxicity was at least 200 times less than that of TX14A-saporin. The cytotoxicity of saporin or conjugated-saporin was also confirmed by microscopic examination of cells. These results indicate that the toxin-conjugate effects can be abrogated by the growth stimulatory peptide, which strongly indicates a receptor-mediated action for the conjugated toxin.

Thus saposin C or TX14A receptors in cancer cells are potential drug targets and are demonstrated herein to inhibit the growth, migration, and invasion of cancer cells. These findings have clear therapeutic implications for those with skill in the art for developing molecular targeted therapies for the treatment of cancer.

EXAMPLE 13

Prosaposin Detection in Tumor Tissue Samples from Prostate Cancer Patients

To assay for prosaposin in tissue samples from prostate cancer patients, formalin-fixed, paraffin-embedded sections were selected from 80 specimens (derived from 80 different individuals): 13 without prostate cancer (including normal prostate cells, benign prostate tumor cells, and BHP cells) and 67 with prostate cancer with a Gleason Sum of 6 to 10 (Gleason Score is a scale used by pathologist to determine the severity of malignancy in a given tumor. The higher the number, the more malignant the tumor is considered). The sections were in the archival tissue storage of Louisiana State University-Health Sciences Center. Staining was done using the Ventana Medical gen II automated immunohistochemical system and reagents (Ventana Medical, Tucson, Ariz.). Formalin-fixed and paraffin-embedded tissues were sliced into 4 μm sections, deparaffinized, and hydrated in xylene and ethanol. Sections were then incubated in 3% hydrogen peroxide for 5 min to eliminate the endogenous peroxidase activity. The sections were then immunostained using the standard DAB kit (Sigma Chemical Co.) with 20% goat serum to prevent nonspecific binding (Santa Cruz Biotech, Santa Cruz, Calif.). After 12 min, the sections were incubated with the primary anti-prosaposin antibody for 32 min, and counterstained with hematoxylin for 4 min.

In all the high grade prostate cancer sections, a high expression of prosaposin was detected. The expression level of prosaposin increased in poorly differentiated and aggressive cancers as measured by the Gleason score. (Data not shown). The prosaposin expression in normal prostate cells or in BPH cells in tissue sections was considerably less than in the prostate cancer cells in malignant cases.

Thus one indicator of the malignancy level of prostate cancer cells is the degree of expression of prosaposin.

The complete disclosures of all references cited in this specification are hereby incorporated by reference. In the event of an otherwise irreconcilable conflict, however, the present specification shall control.

We claim:

1. A ligand/toxin conjugate, comprising a ligand capable of binding a cancer cell receptor that binds saposin C, conjugated to a cytotoxic agent, wherein said ligand is saposin C or a prosaptide of saposin C.

2. A conjugate as in claim 1, wherein said ligand is saposin C.

3. A conjugate as in claim 1, wherein said ligand is a prosaptide.

4. A conjugate as in claim 3, wherein said prosaptide is TX14A.

5. A conjugate as in claim 1, wherein the cytotoxic agent is selected from the group consisting of diphtheria toxin, ricin toxin, abrin toxin, pseudomonas exotoxin, shiga toxin, α-amanitin, pokeweek antiviral protein (PAP), ribosome-inhibiting proteins (RIP), melphalan, methotrexate, nitrogen mustard, doxorubicin, daunomycin, an ionizing radioisotope, and other cytotoxic agents.

6. A conjugate as in claim 5, wherein the cytotoxic agent is a ribosome-inhibiting protein.

7. A conjugate as in claim 6, wherein said cytotoxic agent is saporin.

8. A composition comprising a conjugate as in claim 1, and a physiologically acceptable excipient.

9. A method of inhibiting the metastasis of cancer cells having receptors that bind to saposin C, comprising administering to said cells an effective amount of a conjugate comprising a cytotoxic agent and a ligand, wherein said ligand is saposin C or a prosaptide of saposin C.

10. The method of claim 9, wherein said ligand is saposin C.

11. The method of claim 9, wherein said ligand is a prosaptide.

12. The method of claim 11, wherein said prosaptide is TX14A.

13. The method of claim 9, wherein the cytotoxic agent is selected from the group consisting of diphtheria toxin, ricin toxin, abrin toxin, pseudomonas exotoxin, shiga toxin, α-amanitin, pokeweek antiviral protein (PAP), ribosome-inhibiting proteins (RIP), melphalan, methotrexate, nitrogen, doxorubicin, daunomycin, ionizing radioisotope, and other cytotoxic agents.

14. The method of claim 13, wherein the cytotoxic agent is a ribosome-inhibiting protein.

15. The method of claim 14, wherein the ribosome-inhibiting protein is saporin.

16. The method of claim 9, wherein the metastatic cancer is selected from a group consisting of prostate cancer, breast cancer, lung cancer, and colon cancer.

17. The method of claim 16, wherein the metastatic cancer is prostate cancer.

* * * * *